United States Patent
Shanbhag et al.

(10) Patent No.: US 12,263,017 B2
(45) Date of Patent: Apr. 1, 2025

(54) PLANE SELECTION USING LOCALIZER IMAGES

(71) Applicant: General Electric Company, Schenectady, NY (US)

(72) Inventors: Dattesh Dayanand Shanbhag, Bangalore (IN); Chitresh Bhushan, Schenectady, NY (US); Arathi Sreekumari, Bangalore (IN); Andre de Almeida Maximo, Rio de Janeiro (BR); Rakesh Mullick, Bangalore (IN); Thomas Kwok-Fah Foo, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 1340 days.

(21) Appl. No.: 16/051,723

(22) Filed: Aug. 1, 2018

(65) Prior Publication Data

US 2020/0037962 A1    Feb. 6, 2020

(51) Int. Cl.
*A61B 5/00* (2006.01)
*A61B 5/055* (2006.01)

(52) U.S. Cl.
CPC .......... *A61B 5/7267* (2013.01); *A61B 5/0037* (2013.01); *A61B 5/004* (2013.01); *A61B 5/055* (2013.01); *A61B 5/7425* (2013.01); *A61B 2576/00* (2013.01)

(58) Field of Classification Search
CPC ..... A61B 5/7267; A61B 5/0037; A61B 5/004; A61B 5/055; A61B 5/7425; A61B 2576/00; G06T 7/70; G06T 2207/20081; G06T 2207/20084; G06T 7/0012; G06T 7/11

See application file for complete search history.

(56) References Cited

U.S. PATENT DOCUMENTS

| | | | |
|---|---|---|---|
| 7,490,085 B2 | 2/2009 | Walker et al. | |
| 7,561,910 B2 | 7/2009 | Faber et al. | |
| 7,648,460 B2 | 1/2010 | Simopoulos et al. | |
| 7,715,521 B2 | 5/2010 | Sakaida et al. | |
| 7,876,938 B2 | 1/2011 | Huang et al. | |

(Continued)

FOREIGN PATENT DOCUMENTS

| | | |
|---|---|---|
| WO | 2016182551 A1 | 11/2016 |
| WO | 2018009405 A1 | 1/2018 |
| WO | 2018015414 A1 | 1/2018 |

OTHER PUBLICATIONS

Kim, K. H., et al. (2018). Improving resolution of MR images with an adversarial network incorporating images with different contrast. Medical physics, 45(7), 3120-3131 (Year: 2018).*

(Continued)

*Primary Examiner* — John D Li
(74) *Attorney, Agent, or Firm* — Fletcher Yoder, P.C.

(57) ABSTRACT

The present disclosure relates to use of a workflow for automatic prescription of different radiological imaging scan planes across different anatomies and modalities. The automated prescription of such imaging scan planes helps ensure contiguous visualization of the different landmark structures. Unlike prior approaches, the disclosed technique determines the necessary planes using the localizer images itself and does not explicitly segment or delineate the landmark structures to perform plane prescription.

11 Claims, 16 Drawing Sheets

(56) References Cited

U.S. PATENT DOCUMENTS

| | | | |
|---|---|---|---|
| 8,144,955 B2 | 3/2012 | Bystrov et al. | |
| 8,160,322 B2 | 4/2012 | Dikmen et al. | |
| 8,160,341 B2 | 4/2012 | Peng et al. | |
| 8,190,232 B2 | 5/2012 | Zhang et al. | |
| 8,363,918 B2 | 1/2013 | Schwing et al. | |
| 8,396,268 B2 | 3/2013 | Zabair et al. | |
| 8,565,505 B2 * | 10/2013 | Bergmans | G01R 33/543 |
| | | | 600/407 |
| 8,724,866 B2 | 5/2014 | Wu et al. | |
| 8,781,552 B2 | 7/2014 | Lu et al. | |
| 8,938,113 B2 | 1/2015 | Kovalan et al. | |
| 9,189,866 B2 | 11/2015 | Poole et al. | |
| 9,390,502 B2 | 7/2016 | Dabbah et al. | |
| 9,460,360 B2 | 10/2016 | Han | |
| 9,569,736 B1 | 2/2017 | Ghesu et al. | |
| 9,704,300 B2 * | 7/2017 | Reda | G06T 19/20 |
| 9,846,938 B2 | 12/2017 | Steigauf et al. | |
| 10,429,478 B2 * | 10/2019 | Wang | G01R 33/5635 |
| 2013/0136329 A1 | 5/2013 | Tao et al. | |
| 2013/0336553 A1 | 12/2013 | Buisseret et al. | |
| 2014/0336504 A1 * | 11/2014 | Zhang | A61B 6/505 |
| | | | 600/425 |
| 2015/0238148 A1 | 8/2015 | Georgescu et al. | |
| 2016/0048741 A1 | 2/2016 | Nguyen et al. | |
| 2016/0328643 A1 | 11/2016 | Liu et al. | |
| 2017/0071470 A1 * | 3/2017 | Cetingul | G16H 50/50 |
| 2018/0035892 A1 * | 2/2018 | Lu | A61B 5/0037 |
| 2019/0021625 A1 * | 1/2019 | Reda | G01R 33/543 |
| 2021/0201526 A1 * | 7/2021 | Moloney | G06N 3/082 |

OTHER PUBLICATIONS

Asaei, Ali, et al.; "Brain MRI Landmark Identification and Detection", Department of Electrical and Computer Engineering State University of New York, pp. 1-51, Dec. 2015.

Zhang, Jun, et al.; "Detecting Anatomical Landmarks From Limited Medical Imaging Data Using Two-Stage Task-Oriented Deep Neural Networks", IEEE Transactions on Image Processing, vol. 26, Issue: 10, pp. 4753-4764, Oct. 2017.

Liu, Jin, et al.; "Applications of deep learning to MRI images: A survey", Big Data Mining and Analytics, vol. 01, Issue: 01, pp. 1-18, Mar. 2018.

European Application No. 19188484.0 filed Jul. 25, 2019—European extended Search Report issued Jan. 15, 2020; 10 pages.

Jason Polzin; "Intelligent Scanning Using 1,10 Deep Learning for MRI—TensorFlow—A Medium"; Mar. 1, 2019 (Mar. 1, 2019), pp. 1-8, XP055643214; [https://medium.com/tensorflow/intelligent-scanning-using-deep-learning-for-mri-36dd620882c4]; 8 pages.

* cited by examiner

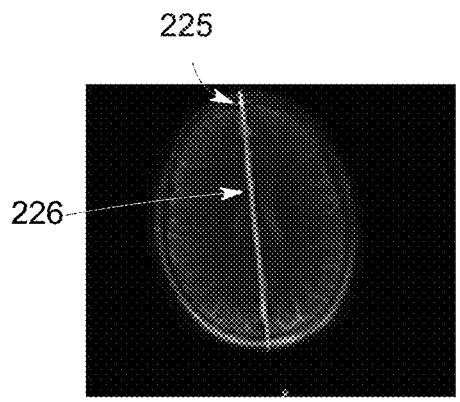
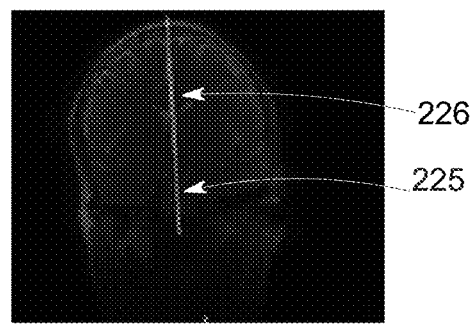
FIG. 9A            FIG. 9B
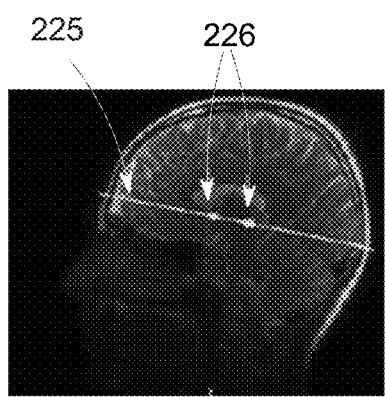
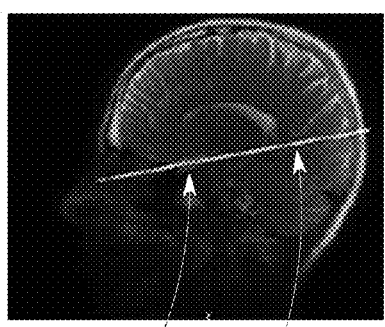
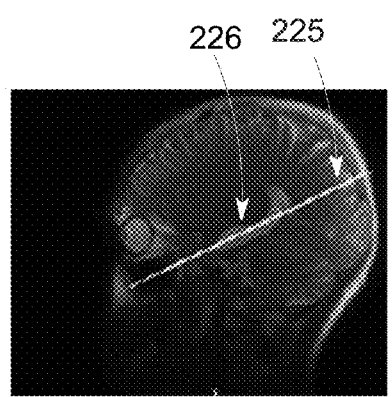
FIG. 9C            FIG. 9D            FIG. 9E

PLANE SELECTION USING LOCALIZER IMAGES

TECHNICAL FIELD

The subject matter disclosed herein relates to non-invasive acquisition of images using localizer images.

BACKGROUND

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

Imaging a patient in a medical context typically involves non-invasively acquiring data of an anatomic region-of-interest (i.e., scanning the patient at the anatomic region-of-interest) and reconstructing the acquired data into an image. As part of this process, it may be useful to initially acquire localizer or scout images that help a reviewer relate a current scanner geometry with the anatomy-of-interest of the patient. However, such localizer or scout images are typically of lower quality and/or resolution than the diagnostic images to be acquired and may be difficult to interpret and properly relate to the proposed scan process and patient anatomy.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a method for imaging an anatomic region is provided. In accordance with this method, a plurality of localizer or scout images are acquired using an imaging system. The plurality of localizer or scout images are provided to a localizer network trained to select a subset of the localizer or scout images for detection and visualization of an anatomic landmark-of-interest based on the image contents of the subset of localizer images. The subset of localizer or scout images or an image construct generated from the localizer or scout images are processed using a scan plane network trained to determine one or more image scan planes or image scan plane parameters that contain regions of the anatomic landmark-of-interest. One or more diagnostic images are acquired using the one or more image scan planes or image scan plane parameters that incorporates the anatomy-of-interest that is necessary to provide a clinical diagnostic assessment.

In a further embodiment, an imaging system is provided. In accordance with this embodiment, the imaging system comprises a memory encoding processor-executable routines for determining one or more imaging scan planes and a processing component configured to access the memory and execute the processor-executable routines. The routines, when executed by the processing component, cause the processing component to: acquire a plurality of localizer or scout images; process the plurality of localizer or scout images using a localizer network trained to select a subset of the localizer or scout images for detection and visualization of an anatomic landmark-of-interest based on the image contents of the subset of localizer or scout images; process the subset of localizer or scout images or an image construct generated from the localizer images using a scan plane network trained to determine one or more image scan planes or image scan plane parameters that contain regions of the anatomic landmark-of-interest; and acquire one or more images using the one or more image scan planes or image scan plane parameters that incorporates the anatomy-of-interest that is necessary to provide a clinical diagnostic assessment.

In an additional embodiment, a method for assessing an imaging scan plane prescription is provided. In accordance with this method, localizer or scout images are acquired using an imaging system. The localizer or scout image data is provided to a neural network trained to generate synthetic image data at a resolution greater than the localizer data. The synthetic image data is reformatted based on an image scan plane prescription to generate reformatted synthetic image data. Feedback related to the reformatted synthetic image data is received. Based upon the feedback, the image scan plane prescription is modified to generate a modified image scan plane prescription. One or more diagnostic images are then acquired using the modified image scan plane prescription.

In another additional embodiment, a method for imaging an anatomic region based on the acquired three-dimensional localizer or scout image volume is provided. In accordance with this method, a plurality of two-dimensional localizer or scout images acquired using an imaging system is combined in a localizer or scout volume. The generated localizer or scout volume is processed using a scan plane network trained for three-dimensional data to determine one or more image scan planes or image scan plane parameters. One or more diagnostic images are then acquired using the one or more image scan planes or image scan plane parameters.

In another embodiment, the localizer network, and the scan plane network, as examples of neural networks, are trained using image data that has been curated such that the networks are able to efficiently and accurately identify different anatomical landmarks in subsets of images presented to the relevant networks. In this manner, the subset of localizer or scout images that contain the anatomical landmarks-of-interest can be correctly identified. Subsequently, further neural networks, such as the scan plane network, may be used to determine a scan plane that results in reformatted images that contain the anatomical landmarks-of-interest in as close to a single scan plane as possible. The scan plane network may consist of a plurality of neural networks where each network is tasked to identify a specific anatomic landmark or several anatomic landmarks.

As discussed herein, the training of the neural networks may utilize as an input image data that has been curated. The curation is typically performed manually where a trained individual, such as a clinician, manually marks the relevant anatomic landmarks in each input image. Another typical procedure that is used to curate the data uses a pre-defined anatomic atlas to automatically curate the input images. The disadvantages of these approaches are that they are not efficient, as in the case of manual curation, or are restricted by the completeness of the anatomic atlas that is used for automated curation.

Unlike these other methods, an embodiment of automated curation as discussed herein does not require the use of a pre-determined anatomical atlas but may instead utilize images that have been pre-determined or assumed to have the correct scan planes that encompass the correct relevant anatomical landmarks. Such an approach may involve the use of a set of images that include the localizer or scout images, and also diagnostic images. The diagnostic images of the correct scan planes will have the necessary information, relative to the localizer or scout images that facilitates an automated curation approach that can then be used for training the neural networks.

In another embodiment of the automated curation, a feature recognition or image segmentation algorithm can be used to process and pre-select images that may then be used for training the neural network such that they contain the relevant anatomical landmarks-of-interest. In this manner the correct imaging scan planes can be identified from these images and used for training the neural networks.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIGS. 9A, 9B, 9C, 9D, and 9E depict examples of ground truth images, in accordance with aspects of the present disclosure;

DETAILED DESCRIPTION

Figure 1:
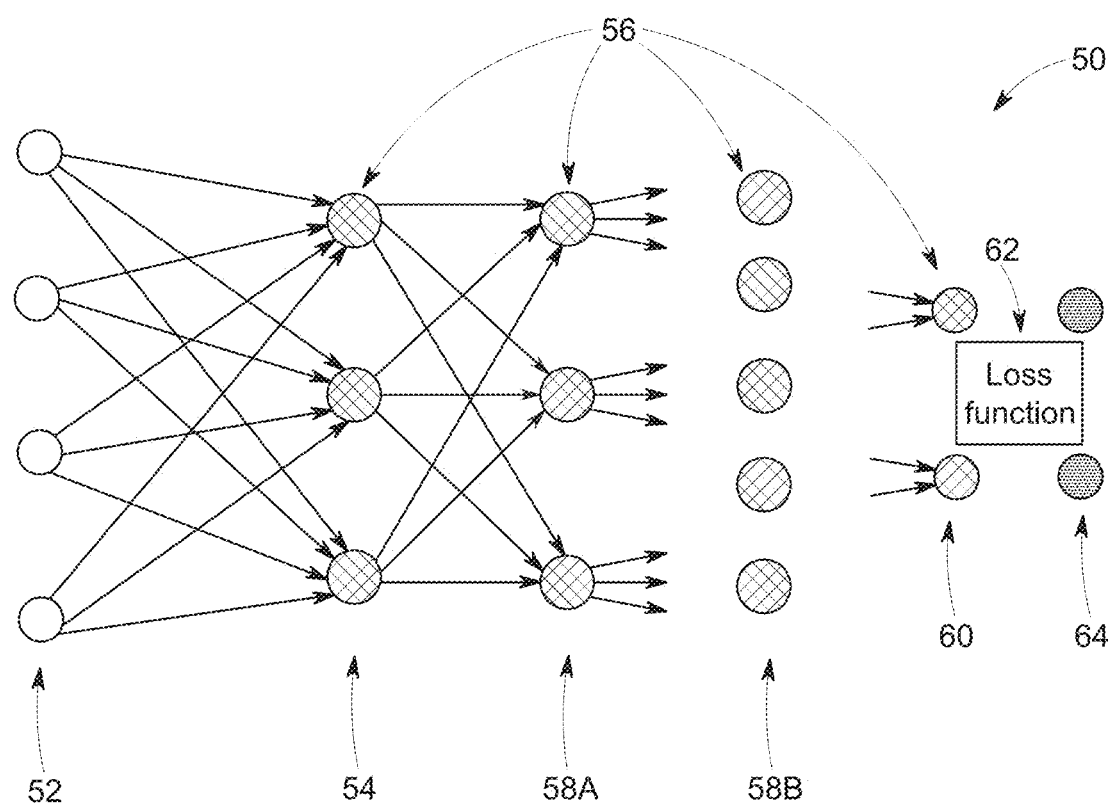
FIG. 1 depicts an example of an artificial neural network for training a deep learning model, in accordance with aspects of the present disclosure.
Figure 2:
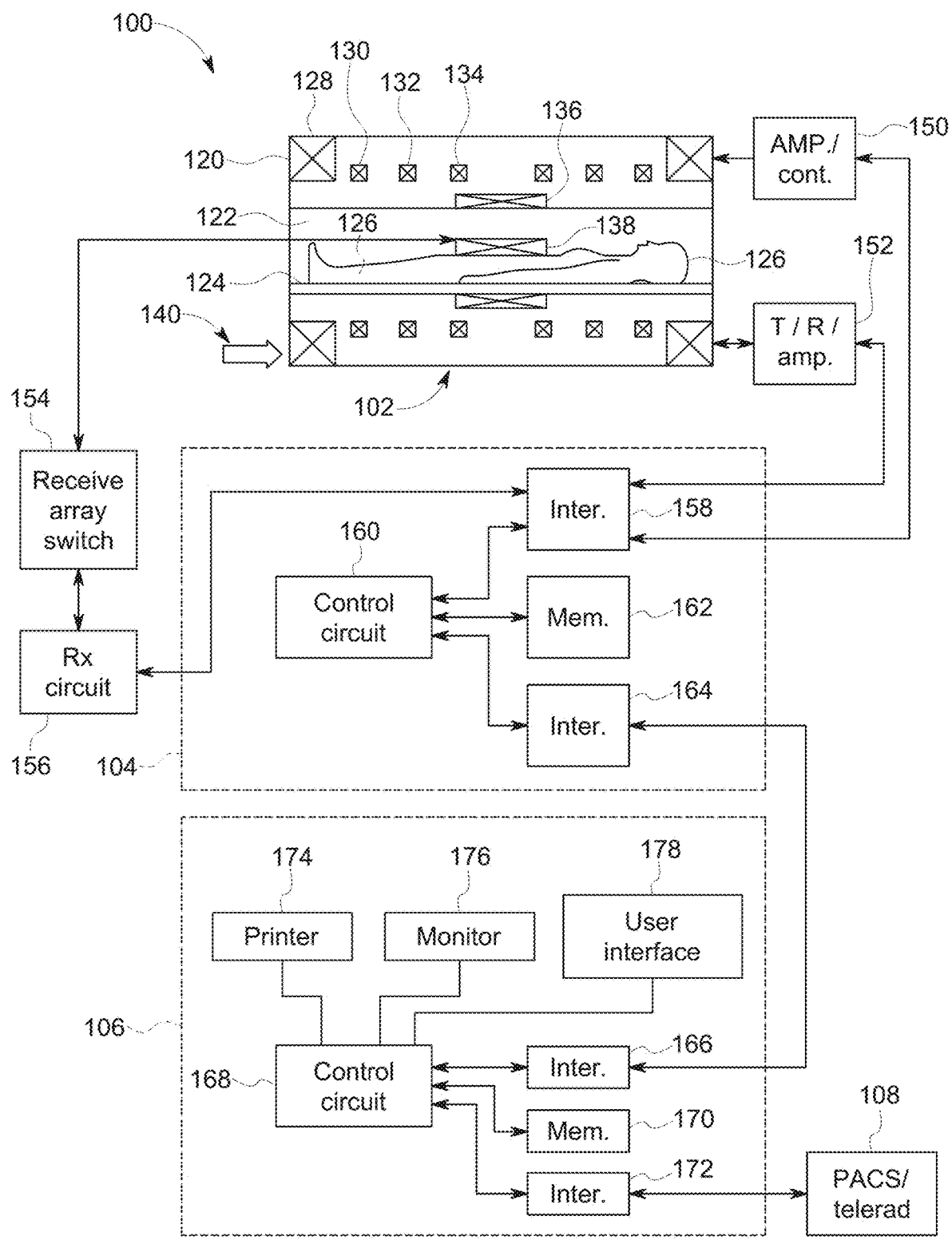
FIG. 2 illustrates an embodiment of a magnetic resonance imaging (MRI) system suitable for use with the disclosed technique.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing field where a set or type of acquired data undergoes a reconstruction process to generate an image or volume.

Further, though magnetic resonance imaging (MR or MRI) examples are primarily provided herein, it should be understood that the disclosed techniques may be used in other imaging modality contexts. For instance, the presently described approach may also be employed on data acquired by other types of scanners employing initial, non-diagnostic images for localization purposes (e.g., localizer or scout images), including, but not limited to, computed tomography (CT) or positron emission tomography (PET)-MR scanners as well as others.

With this in mind, and as discussed herein, the present disclosure relates to use of an artificial intelligence-based workflow for automatic prescription of different radiological imaging scan planes using one or more initial (e.g., localizer or scout) images. The goal of the automated prescription of such imaging scan planes is to ensure contiguous visualization of the different anatomical landmark structures relevant to a given examination or the inclusion of one or more anatomical landmark structures within a given imaging plane that facilitates easier or more efficient diagnostic assessment for a given examination. Unlike prior approaches, the present disclosure: (a) determines the necessary imaging scan planes using the localizer or scout images itself; (b) does not explicitly segment or delineate the landmark structures within the localizer images to perform plane prescription; and (c) guides or provides visualization to the user to the anatomical landmark slice, scan plane or region on the localizer or scout images itself. In addition, the deep learning-based techniques discussed herein speed the processing time by allowing single shot multi-plane determination as well as matching the input data to the training data used for deep learning model generation to improve prescription accuracy. In practice, different or specially trained neural networks may be employed for different categories of patients (e.g., based on age, gender, pre-diagnosed condition, height, weight, and so forth), different procedures (e.g., neurological, cardiac, orthopedic, angiographic, and so forth), and/or different anatomy (e.g, brain, heart, knee, shoulder, spine, vasculature, whole-body scan planning, and so forth).

With the preceding introductory comments in mind, some generalized information is provided to provide both general context for aspect of the present disclosure and to facilitate understanding and explanation of certain of the technical concepts described herein.

For example, as noted above, deep-learning approaches may be employed with respect to automatically determining one or more imaging scan planes relevant to anatomical landmarks-of-interest. The one or more scan planes may be determined using initial localizer or scout images, and without requiring segmentation of the anatomical landmarks within the localizer images. Deep learning approaches discussed herein may be based on artificial neural networks, and may therefore encompass deep neural networks, fully connected networks, convolutional neural networks (CNNs), perceptrons, auto encoders, recurrent networks, wavelet filter banks, or other neural network architectures. These techniques are referred to herein as deep learning techniques, though this terminology may also be used specifically in reference to the use of deep neural networks, which is a neural network having a plurality of layers.

As discussed herein, deep learning techniques (which may also be known as deep machine learning, hierarchical learning, or deep structured learning) are a branch of machine learning techniques that employ mathematical representations of data and artificial neural networks for learning and processing such representations. By way of example, deep learning approaches may be characterized by their use of one or more algorithms to extract or model high level abstractions of a type of data-of-interest. This may be accomplished using one or more processing layers, with each layer typically corresponding to a different level of abstraction and, therefore potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data.

In general, the processing from one representation space to the next-level representation space can be considered as one 'stage' of the process. Each stage of the process can be performed by separate neural networks or by different parts of one larger neural network. For example, as discussed herein, a single deep learning network or multiple networks in coordination with one another may be used to determine image scan planes from localizer images for use in a subsequent image acquisition operation. Such image scan plane determination, as discussed herein, is performed without segmenting the anatomic landmarks-of-interest within the localizer images.

As part of the initial training of deep learning processes to solve a particular problem, training data sets may be employed that have known initial values (e.g., input images, projection data, emission data, magnetic resonance data, and so forth) and known or desired values for a final output (e.g., corresponding image scan planes) of the deep learning process. The training of a single stage may have known input values corresponding to one representation space and known output values corresponding to a next-level representation space. In this manner, the deep learning algorithms may process (either in a supervised or guided manner or in an unsupervised or unguided manner) the known or training data sets until the mathematical relationships between the initial data and desired output(s) are discerned and/or the mathematical relationships between the inputs and outputs of each layer are discerned and characterized. Similarly, separate validation data sets may be employed in which both the initial and desired target values are known, but only the initial values are supplied to the trained deep learning algorithms, with the outputs then being compared to the outputs of the deep learning algorithm to validate the prior training and/or to prevent over-training.

With the preceding in mind, FIG. 1 schematically depicts an example of an artificial neural network 50 that may be trained as a deep learning model as discussed herein. In this example, the network 50 is multi-layered, with a training input 52 and multiple layers including an input layer 54, hidden layers 58A, 58B, and so forth, and an output layer 60 and the training target 64 present in the network 50. Each layer, in this example, is composed of a plurality of "neurons" or nodes 56. The number of neurons 56 may be constant between layers or may vary from layer to layer. Neurons 56 at each layer generate respective outputs that serve as inputs to the neurons 56 of the next hierarchical layer. In practice, a weighted sum of the inputs with an added bias may be computed to "excite" or "activate" each respective neuron of the layers according to an activation function, such as rectified linear unit (ReLU), sigmoid function, hyperbolic tangent function, or otherwise specified or programmed. The outputs of the final layer constitute the network output 60 (e.g., an image scan plane or parameters of such a scan plane) which, in conjunction with a target image 64, are used to compute some loss or error function 62, which will be backpropagated to guide the network training.

The loss or error function 62 measures the difference or similarity between the network output (i.e., a denoised image) and the training target. In certain implementations, the loss function may be a derived mean squared error (MSE). In others it could be the overlap ratio. Alternatively, the loss function 62 could be defined by other metrics associated with the particular task in question, such as a Dice (overlap measure) function or score.

To facilitate explanation of the present image scan plan determination using deep learning techniques, the present disclosure primarily discusses these approaches in the context of an MM system. However, it should be understood that the following discussion may also be applicable to other imaging modalities and systems including, but not limited to computed tomography (CT), as well as to non-medical contexts or any context where localizer images are employed as part of an image acquisition protocol.

With respect to MRI, the disclosed technique may offer certain advantages. For example, MM is inherently a multi-planar and multi-contrast imaging modality. The ability of MRI to acquire imaging data in any arbitrary plane itself makes MM exam planning a complex task, introducing variability in the exams and results in a longer learning curve for MR technologists. For multi-contrast MR imaging, the delay in setting up a single imaging series increases inter-series gap and results in longer duration of the MR exam, especially when multiple landmark data is to be acquired.

To address these issues, the present methodology provides tools to help automatically prescribe the MRI exam without any additional user-interaction or disruption of existing workflow and with minimal processing. In certain implementations, the scan set-up may be completed using multi-plane or three-plane localizer or scout images, without the need for an additional 3D localizer image set or higher resolution imaging data for planning the imaging of finer structures (e.g. the optic nerve or hippocampus in brain). The described method allows this to be accomplished a fast and robust manner, even in presence of pathology or some data corruption. Apart from prescribing the image scan plane, the methodology allows visualization of the image scan plane on the most relevant slice for a given landmark structure and/or customizing the acquisition parameters based on the needed coverage, extent, and orientation. Such customization of acquisition parameters in an MTI context include the imaging field-of-view (FOV), direction of the phase-encoding axis relative to the imaging slice orientation or scan plane, direction of the frequency encoding axis relative to the imaging slice orientation or scan plane, amount of fractional field-of-view, spatial resolution to adequately visualize the anatomical landmark-of-interest, the number of slices or imaging planes needed to adequately visualize the anatomical landmarks-of-interest, or orientation of the imaging scan plane about a perpendicular axis to avoid motion-related artifacts from adjacent anatomy.

With this in mind, the embodiments described herein may be implemented as at least a part of a magnetic resonance imaging (MRI) system, wherein specific imaging routines (e.g., diffusion MRI sequences) are initiated by a user (e.g., a radiologist or other technologist). The MRI system may perform data pre-acquisition (i.e., localizer imaging), primary data acquisition, data construction, and so forth. Accordingly, referring to FIG. 1, a magnetic resonance imaging system 100 is illustrated schematically as including a scanner 102, scanner control circuitry 104, and system control circuitry 106. According to the embodiments described herein, the MRI system 100 is generally configured to perform MR imaging, such as imaging sequences for diffusion imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 to be positioned therein for imaging selected anatomy within the patient.

Scanner 102 includes a series of associated coils for producing controlled magnetic fields for exciting the gyromagnetic material within the anatomy of the subject being imaged. Specifically, a primary magnet coil 128 is provided for generating a primary magnetic field, BO, which is generally aligned with the bore 122. A series of gradient coils 130, 132, and 134 permit controlled magnetic gradient fields to be generated for positional encoding of certain of the gyromagnetic nuclei within the patient 126 during examination sequences. A radio frequency (RF) coil 136 is configured to generate radio frequency pulses for exciting the certain gyromagnetic nuclei within the patient. In addition to the coils that may be local to the scanner 102, the system 100 also includes a set of receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain of the gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, Bo. A power input 44 (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuit 104.

A control circuit 152 is provided for regulating operation of the RF coil 136. Control circuit 152 includes a switching device for alternating between the active and inactive modes of operation, wherein the RF coil 136 transmits and does not transmit signals, respectively. Control circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuit 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the driver circuit 150 and control circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

A second interface circuit 164 is coupled to the control and analysis circuit 160 for exchanging data between scanner control circuit 104 and system control circuit 106. In certain embodiments, the control and analysis circuit 160, while illustrated as a single unit, may include one or more hardware devices. The system control circuit 106 includes an interface circuit 166, which receives data from the scanner control circuit 104 and transmits data and commands back to the scanner control circuit 104. The system control and analysis circuit 168 may include a CPU in a multi-purpose or application specific computer or workstation. System control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data.

An additional interface circuit 172 may be provided for exchanging image data, configuration parameters, and so forth with external system components such as remote access and storage systems or PACS 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

With the preceding discussion of an example MRI system 100 and neural network 50 in mind, as discussed herein such tools may be used to identify image scan planes useful for diagnostic imaging. For example, in one embodiment, a deep learning-based framework is provided for automatically processing one or more localizer images to prescribe radiological imaging scan planes across different anatomies. In one such implementation, the deep learning-based framework uses a cascade of trained neural networks to retain or select relevant localizer or scout images (typically obtained prior to a diagnostic imaging sequence), determine an anatomical coverage or region-of-interest on the selected localizer images, and determine an arbitrary plane for a landmark of diagnostic interest and parameterize the plane (such as by performing plane fitting on a derived plane cloud point). As noted above, different or differently trained neural networks may be employed at these various stages based on patient specific-factors, prescribed procedure, and/or anatomy-of-interest.

With respect to training of the neural networks, since the deep learning-based framework is data dependent an augmentation scheme may be used to generate numerous training examples based on rotation, translations, rotations plus translations, image intensity variations, distortions, artifacts (metal related in MR), MR image intensity bias due to coils, and so forth. In general, augmentation schemes may employ geometrical and physics driven changes to mimic real-clinical data scenarios of deep learning training.

In certain embodiment discussed herein, auto-curated or atlas-based approaches may be used both for initial neural network training and for updating or maintaining network performance. As noted above, for the training data, it may be understood that there is a pre-determined relationship between the input data and the desired outcome. As an example relevant to the present context, if the neural network is to be trained to identify a specific anatomical landmark-of-interest, that anatomical landmark-of-interest is a priori marked or indicated in the input data. The neural network is then trained to identify that specific anatomical landmark-of-interest. In addition, the input data that have no anatomical landmarks-of-interest can also be used as training data to help the neural network discriminate between the presence or absence of the specific anatomical landmarks-of-interest. The step of indicating the desired outcome in the input data is referred to as data curation as it separates out the input data into categories that contain or do not contain the desired outcome.

Whereas traditional data curation relies on time-consuming manual curation in which a trained individual manually sorts through the input data and marks the desired outcome, it is beneficial for ingesting larger amounts of data if the curation could be automated and achieve a high degree of precision. An example of manual data curation in diagnostic imaging is the identification, by a clinician, of anatomical landmarks-of-interest in localizer or scout images.

Other automated curation approaches may use a pre-determined atlas of digital images and attempt to match the input images to the pre-determined atlas to identify landmarks-of-interest. These atlas-based automated curation approaches are limited by the ability to match to a pre-determined atlas and do not perform well when there is a variation or deviation between the atlas and the input images. As an example, when motion or deformation is present, the accuracy of the atlas-based curation approach is decreased. This ultimately impacts the accuracy and precision of the trained neural networks due to poor training data. As such, atlas-based approaches to automated curation perform better in regions of the anatomy where there is little motion or deformation, such as the brain. It does not perform as well in other regions of the anatomy, such as the knee, the abdomen, or the heart where motion and deformation makes matching to a fixed atlas difficult.

With the preceding in mind, an automated curation method that does not rely on atlases or manual curation is described and may be employed in training one or more of the neural networks described herein. One embodiment of the automated curation approach utilizes a set of images consisting of localizer or scout images together with sets of diagnostic images acquired based upon the respective localizer or scout images. As these images have been used for diagnostic assessment and have not been repeated or rescanned, it is understood that the diagnostic images contain the anatomical landmarks-of-interest. As such the imaging scan planes relative to the localizer or scout images can be determined without manual review or intervention or the use of atlas-based matching. In this manner, the input localizer or scout images corresponding to the respective diagnostic images will have the desired outcome indicated automatically as it is ingested into the training data set for training the neural network. This can be done efficiently and with precision for large amounts of data. Furthermore, during diagnostic imaging operations using the trained neural networks, new data generated by the imaging operations can be incorporated in an automated fashion into a larger, growing training data set automatically to augment the training data set used for the initial training of the neural network, thereby continuously improving the accuracy and precision of the neural network.

Another embodiment of the automated curation training approach is to use an image segmentation algorithm that utilizes feature recognition algorithms, such as those used in unsupervised machine learning, to generate the desired outcome in the localizer or scout images used to train the neural networks. In this case, the desired outcome is the determination of the absence or presence of the anatomical landmarks-of-interest. As such the imaging scan planes relative to the localizer or scout images can be determined without manual intervention or the use of atlas-based matching. In this manner, the input localizer or scout images will have the desired outcome indicated automatically as it is ingested into the training data set for training the neural network. This can be done efficiently and with precision for large amounts of data. Furthermore, during the diagnostic imaging operations using the trained neural networks, new data can be incorporated in an automated fashion into a larger, growing training data set automatically to augment the training data set used for the initial training of the neural network, thereby continuously improving the accuracy and precision of the neural network.

Figure 3:
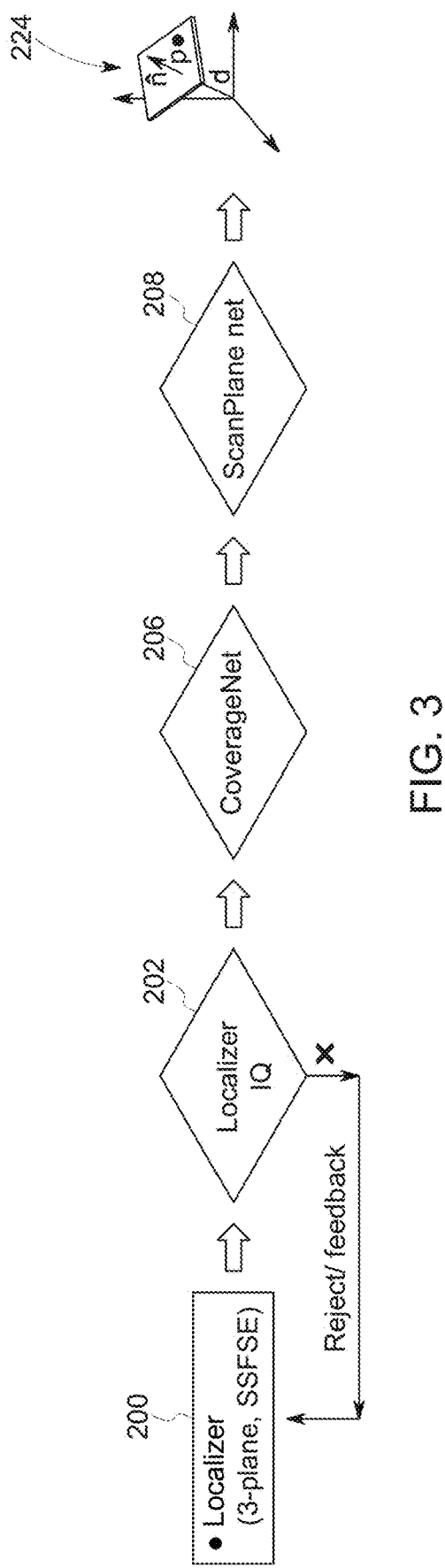
FIG. 3 depicts a high-level overview of a workflow in accordance with aspects of the present disclosure.

With the preceding discussion in mind with respect to neural networks, examples of suitable imaging systems, and suitable neural network training methodologies for certain of the neural networks described herein, FIG. 3 depicts an example of a high-level process flow for one implementation. In this example, localizer images 200 are initially acquired and provided to a trained localizer network 202 (here illustrated as the Localizer IQ network) for processing. As used herein, the localizer or scout images 200 may be acquired as part of a pre-acquisition step in which current patient and scanner geometry may be evaluated so as to determine a relevant image scan plane that may be used in acquiring subsequent diagnostic images-of-interest.

For example, in certain implementations, the localizer or scout images 200 may be one or more offset planar images, such as three or more single-shot, fast spin echo (SSFSE) images, acquired in what is generally believed to be or estimated to be the diagnostic region-of-interest. Due to the localizer or scout images 200 being taken without exact knowledge of the region actually being targeted by the current acquisition geometry (but with the expectation that the region-of-interest is being targeted or is proximate to at least one of the localizer or scout images 200) some or all of the localizer images 200 may not depict the anatomy-of-interest, may be noise, and/or may be at a poor orientation to the anatomic region-of-interest. Likewise, the localizer or scout images 200 may be acquired without exact knowledge of the orientation of the acquisition with respect to the region-of-interest. By way of example, for a brain examination sequence, three-plane localizer or scout images 200 for a brain exam may the target anatomic structures, may contain non-brain (i.e., non-target) anatomy and/or may be noise slices, as a result of the localizer or scout image acquisition being blind to the anatomical coverage.

As shown in FIG. 3, in the depicted example the localizer or scout images 200 are provided to a trained localizer network 202 (here illustrated as the Localizer IQ network) for processing. In this example, the localizer network 202 identifies data relevant to the anatomy-of-interest (i.e., the prescribed anatomy) and/or structures associated with an anatomic landmark associated with the prescribed image acquisition. In particular, the localizer network 202 may be characterized as determining or identifying image data appropriate for processing by a downstream anatomy engine (discussed below) and as identifying the best image(s) (i.e., slice or slices) for subsequent landmark detection and visualization.

Figure 4:
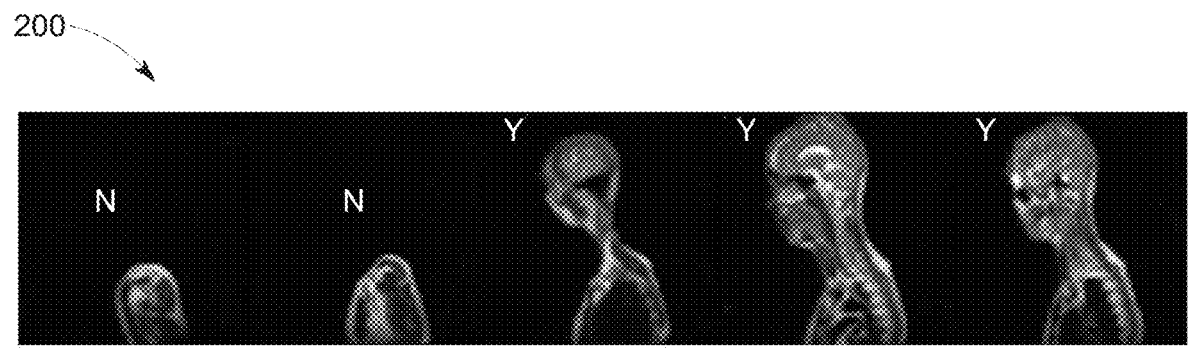
FIG. 4 depicts a sequence of offset localizer images or scout, in accordance with aspects of the present disclosure.

For example, data identified by the localizer network 202 that is relevant to the anatomy-of-interest and/or structures associated with anatomic landmark is used to tag the relevant localizer image slices (e.g., brain slices) for downstream processing. In certain implementations, the localizer network 202 labels the correct localizer or scout image(s) 200 for use by subsequent networks for diagnostic image sequence planning and parameterization, such as indicating a localizer or scout image 200 for use that has the maximal or optimal coverage of the anatomy or landmark-of-interest. For example, in a spine imaging context, a localizer or scout image with maximum spine coverage may be automatically tagged for use by the downstream networks. By way of illustration, and turning to FIG. 4, a sequence of offset localizer or scout images 200 (i.e., slices) acquired for a brain scan are shown. In this example, the first two images capture only a patient shoulder (i.e., are out of plane with the skull) and are therefore rejected as not capturing the anatomy-of-interest. The last three images, conversely, capture portions of the brain and therefore are acceptable for further processing as depicting the anatomy-of-interest.

Figure 5:
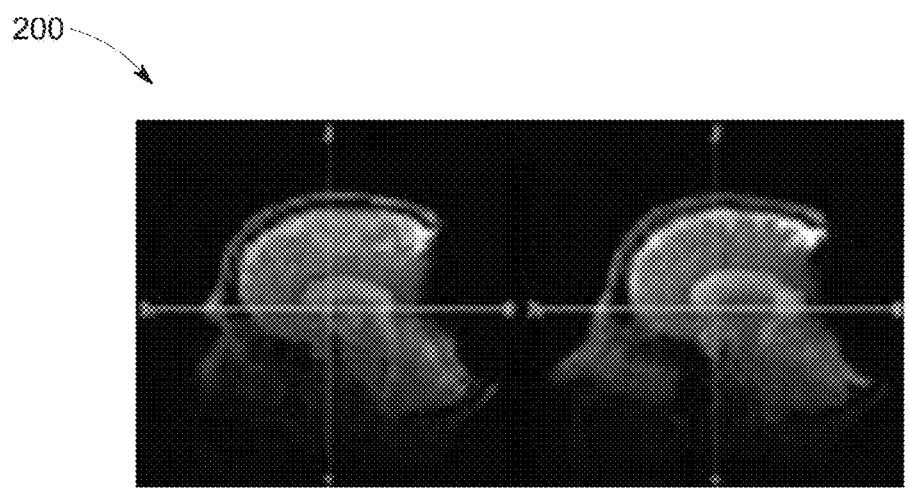
FIG. 5 depicts a pair of localizer or scout images exhibiting artifacts, in accordance with aspects of the present disclosure.

If no suitable data is identified or if the data is ambiguous, the localizer or scout images 200 may be rejected or additional/alternative localizer or scout images 200 requested, as shown. For example, in the presence of metal, localizer or scout images 200 may exhibit large or substantial metal-related artifacts, making them unfit for scan plane determination. By way of example, FIG. 5 depicts a pair of localizer or scout images 200 acquired for a brain scan that are of the anatomy-of-interest, but which exhibit substantial artifacts that make the images unacceptable for further processing. Such localizer image data may be rejected and feedback provided to user. Similarly, in knee-imaging contexts, it is possible that technician provides erroneous information during the exam set-up (e.g., indicating a head first orientation when the patient was in-fact scanned feet first). Consequently, the images will be in-correctly represented in scanner geometry space and as such they are tagged before being used for location and orientation determination.

In the depicted example, the localizer network 202 provides the identified relevant set of localizer images to a second trained neural network, here denoted the coverage network 206 or Coverage Net, that is trained to identify the gross imaging field-of-view (i.e., center of FOV and the extent) for the relevant anatomy. Thus, in this example, the second trained neural network determines location and coverage of the feature-of-interest in the localizer or scout images 200 identified or selected by the first trained network. By way of example, the coverage network 206 may process the localizer or scout image(s) 200 (or data derived from the localizer or scout images 200) to estimate or predict an anatomic mask (e.g., a brain mask) that corresponds to the desired or needed coverage for a given scan. As discussed herein, in one implementation, the coverage network 206 may generate the anatomic mask by predicting a signed distance transform for the anatomy which is then thresholded and through a shape encoder to provide the binary mask.

It may be noted that the input to the coverage network 206 may be the two-dimensional (2D) localizer or scout images themselves or, alternatively, the stack of 2D localizer images may be treated as a three-dimensional (3D) volume and processed by the coverage network 206 or a fused single 3D image or a stack of 2D images from a 3D volume acquisition may be generated from the localizer or scout image and processed by the coverage network 206. As may be appreciated, use of fused images may allow for completion of the orthogonal plane data in each of the axial, sagittal, and coronal planes, however with a trade-off in terms of increased computational complexity and processing time. As may be appreciated, in certain of the implementations in which the coverage network is processing a 3D input, as opposed to a 2D input, a 3D convolutional neural network may be employed as opposed to a 2D convolutional neural network.

In one implementation, the coverage network 206 (and scan plan network 208 discussed below) may be trained using ground truth data generated be performing non-rigid mapping between high-resolution images (e.g., T1 weighted (T1W) MM volumes) to corresponding T1W atlas images and transferring the labels to corresponding T1W and localizer images.

Figure 6:
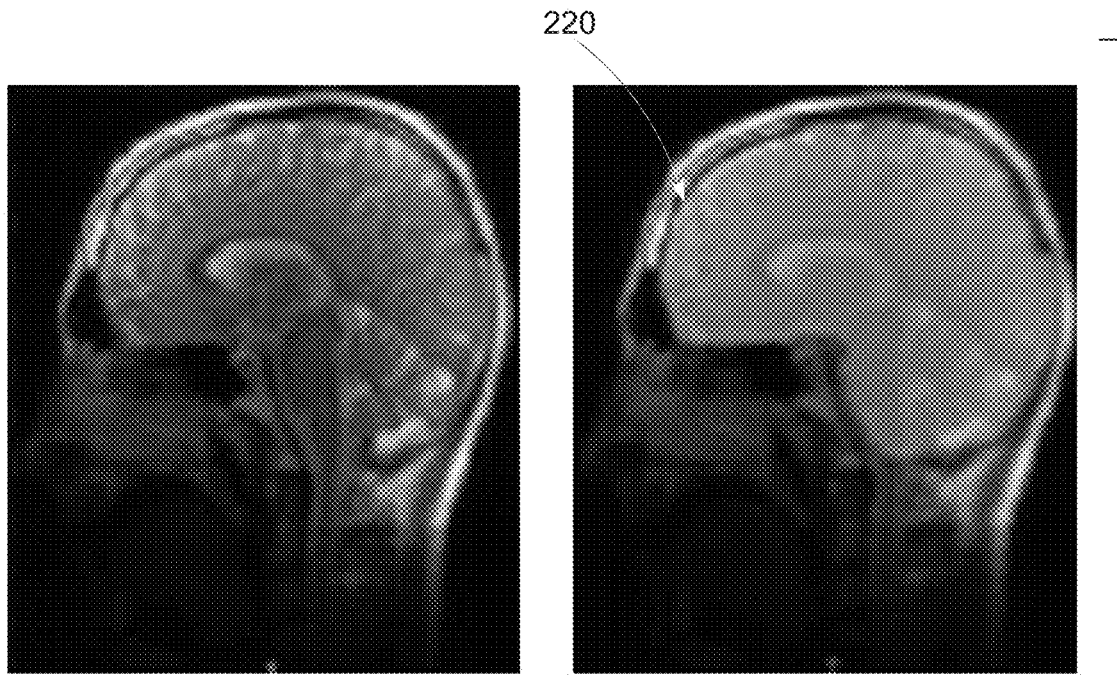
FIG. 6 depicts a brain scan image and derived mask, in accordance with aspects of the present disclosure.
Figure 7:
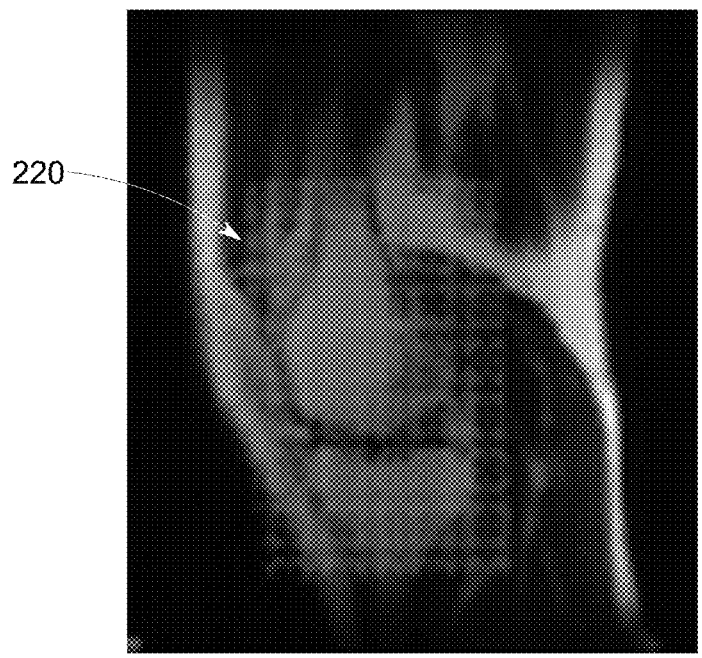
FIG. 7 depicts a knee scan image and derived mask, in accordance with aspects of the present disclosure.

By way of illustrating operation of the coverage network, FIG. 6 depicts a brain scan image in which the location and coverage of the brain (i.e., the anatomic region-of-interest) is not determined (leftmost image) and an image process by a trained coverage network 206 in which the brain location and coverage or extent in the image has been determined (rightmost image) as a mask 220. Based on this, the center of the field-of-view and the extent of coverage with respect to the anatomy-of-interest (i.e., the gross imaging field-of-view) may be defined, such as based on the mask 220. An additional example is provided in FIG. 7, where a knee is the anatomy-of-interest. In the depicted example, the relevant gross imaging field-of-view (mask 220) corresponding to the location and extent of the anatomy-of-interest is identified.

Based on the identified imaging field-of-view, the orientation of the field-of-view bounding box is determined. In the depicted example, the orientation is determined by a third trained neural network (herein denoted as a scan plan network 208 and illustrated in FIG. 3 as ScanPlane Net) which, based on the determined orientation, localization, and coverage within the processed localizer or scout images 200, outputs one or more image scan planes or image scan plane parameters by fitting an analytic plane to one or more landmark structures present in the localizer or scout images 200. While the example illustrated in FIG. 3 describes the scan plan network 208 processing the output of the coverage network 206 (e.g., a mask image 220 or the signed distance transform of the mask), in practice the scan plane network 208 may instead be trained to work directly on the localizer or scout images 200 (or images or constructs derived from the localizer or scout images 200.

In certain implementations, the scan plan network 208 generates the imaging scan plane(s) 224 by one or more of segmenting the plane as a binary mask and fitting the plane to the mask point cloud or by directly generating the plane parameters from the localizer or scout images 200 or previously determined field-of-view region (i.e., mask image 220 in the preceding examples). Thus, the scan plan network 208 as discussed herein may output: (1) one or more imaging scan planes (such as in the form of a fitted segmentation mask) to be used in a subsequent scanning operation and/or (2) parameters defining or describing one or more such imaging scan planes to be used in a subsequent scanning operation.

Figure 8:
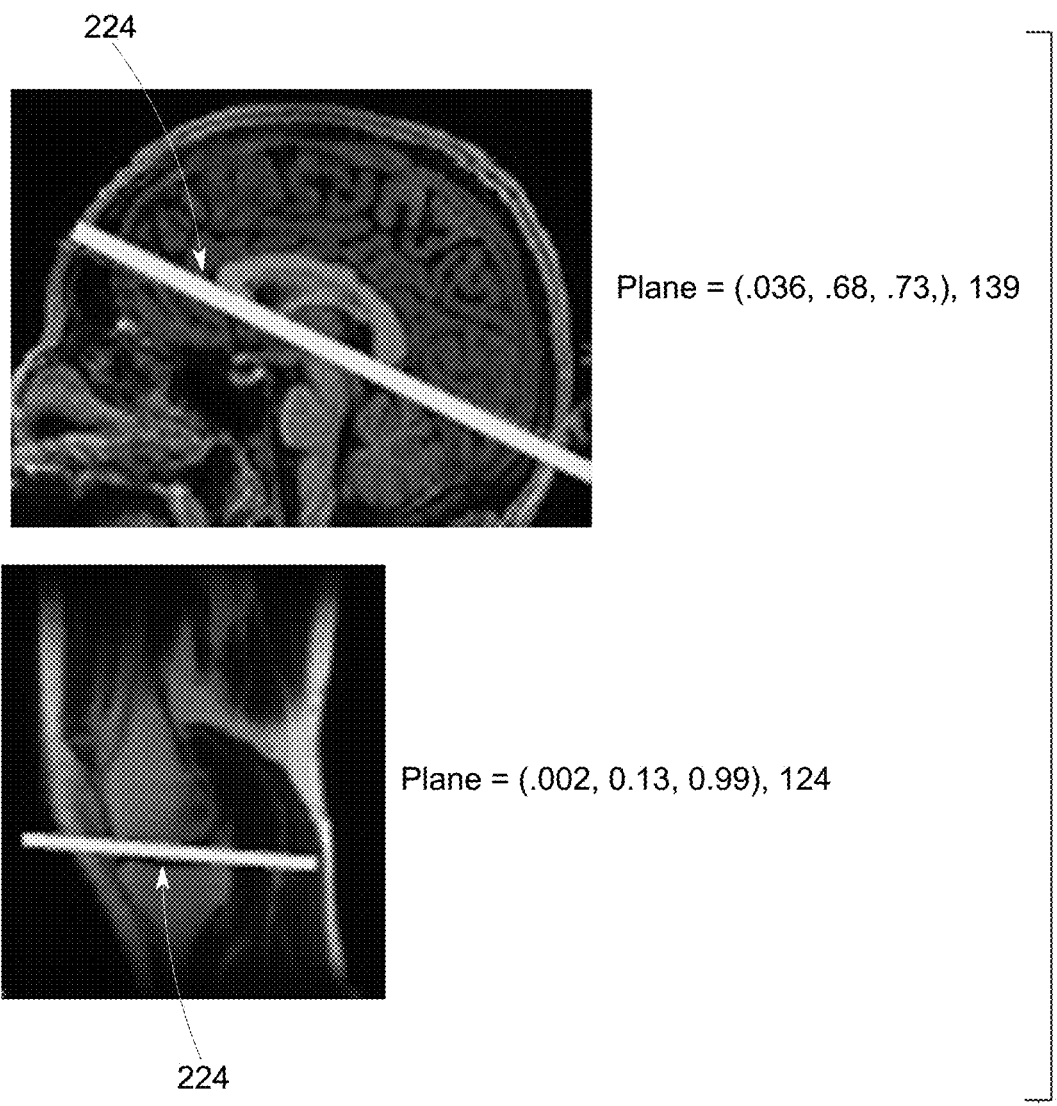
FIG. 8 depicts imaging scan planes and associated parameters, in accordance with aspects of the present disclosure.

Examples of such determined imaging scan planes 224 and their localization and orientation parameters are shown in FIG. 8, with the topmost image illustrating a determined imaging scan plane for a brain scan and the bottommost image illustrating a determined imaging scan plane for a knee scan.

As noted above, in one embodiment the scan plan network 208 may be trained using ground truth data generated be mapping between high-resolution images (e.g., T1 weighted (T1W) MRI volumes) to corresponding T1W atlas images and transferring the labels to corresponding T1W and localizer images. To clarify aspects of this training approach, various examples of ground truth images are provided in FIGS. 9A through 9E. In these examples, FIGS. 9A and 9B depict a fitted mid-sagittal plane mask as a landmark structure 226 to which an analytic plane 225 is fitted; FIG. 9C depict the labeled anterior commissure and posterior commissure as landmark structures 226 to which an analytic plane 225 is fitted; FIG. 9D depicts a labeled optic nerve as a landmark structure 226 to which an analytic plane 225 is fitted; and FIG. 9E depicts a labeled hippocampus as a landmark structure 226 to which an analytic plane 225 is fitted.

It is worth noting that, though the landmark structures used to fit a given plane may be labeled and annotated in the ground truth images used to train a given scan plan network 208, in certain implementations such structures or landmarks are not segmented and/or labeled during operation, with the trained scan plan network 208 instead placing the plane-of-interest based on the whole or un-segmented localizer image. This is in contrast to conventional techniques in which reference structures or landmarks are explicitly segmented and/or labeled in an image as part of image scan plane placement.

As discussed above, in other embodiments an auto-curation approach may be employed with respect to training the scan plane network 208 (or other neural networks as discussed herein, such as the localizer network 202. In such an embodiment, the automated curation approach utilizes a set of images consisting of localizer or scout images together with sets of diagnostic images acquired based upon the respective localizer or scout images 200. In this approach, it may be assumed that the images used for diagnostic assessment contain the anatomical landmarks-of-interest and that the clinical prescription was correct. In practice, the prescription may be available in the header (e.g., DICOM header) of the diagnostic image. Thus, a training pair may consist of the localizer or scout image(s) along with the diagnostic image acquired using the localizer or scout images 200, which have the image scan plane prescription encoded in the header of the image file. Therefore, the imaging scan plane(s) relative to the localizer or scout images 200 can be determined without manual review or intervention or the use of atlas-based matching.

Figure 10:
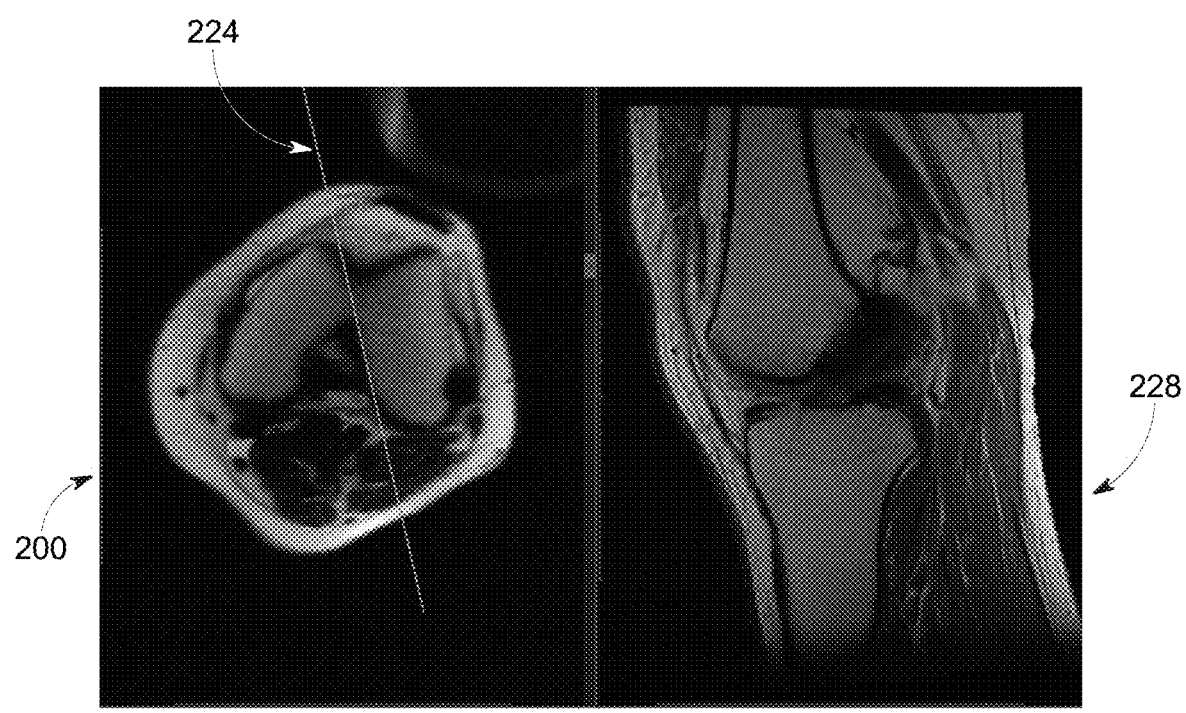
FIG. 10 depicts a training image pair including a localizer image and diagnostic image, in accordance with aspects of the present disclosure.

An example of such a pair of training images (i.e., a localizer image 200 and diagnostic image 228 acquired based upon the respective localizer image) are illustrated in FIG. 10. As noted above, the diagnostic image 228 (here a high-resolution sagittal clinical image) is acquired at a known image scan plane 224 determined with respect to the localizer image 200 (here an axial localizer image), where the image scan plane prescription is available from the diagnostic image header or metadata. Thus, the header image information from the diagnostic image 228 may be used to automatically determine the image scan plane-of-interest with respect to the localizer image. The scan plane network 208 can then be trained using the binary plane mask or image scan plane parameters.

While the preceding provides a high-level overview of aspects of the disclosed techniques, certain implementations are discussed below to provide further examples and technical detail with respect to the networks described above.

With respect to the localizer network 202, in one implementation, the localizer network 202 may be implemented with one or more sub-network levels or constituents. For example, an image stratification sub-network may be provided as part of the localizer network 202 to classify or sort localizer images into good slices and extreme or unacceptable slices and to provide the rejection or feedback indications based on the classification or sorting process.

Similarly, an image field-of-view cutoff network may be provided as part of the localizer network 202. In particular, the field-of-view coverage of the organ under study may differ across demographic groups and/or across different age-groups. To address this, a field-of-view cutoff network may be employed to automatically determine the cut-off of the localizer field-of-view coverage so that localizer images 200 match the training data for the downstream coverage network 206 and scan plan network 208. For example, in a pediatric brain scan context, the pediatric examination scans may exhibit fields-of-view extending to the neck. In such a context, the field-of-view cutoff network may truncate the localizer images 200 along the superior-inferior (SI) axis to correspond with the coverage network 206 and scan plan network 208 training data cohort. For example, the training data may be sagittal cranial images with ground truth indications (provided by radiologist annotation) of the transition from head to neck in the SI direction. In testing, the trained network may be used to predict the SI head to neck transition point in test sagittal images. In such a scenario, the neural network trained using sagittal images can be used in determining field-of-view cutoff in both sagittal and coronal images. Selected localizer images 200 truncated by such a neural network may then be passed to the coverage network 206 and scan plan network 208 for processing.

With respect to the processing performed by the localizer network 202, for a given scan or examination type, a limited number of classes of images may be established into which the provided localizer or scout images 200 may be classified. By way of example, in the context of a brain scan, localizer or scout images 200 may be sorted into classes corresponding to: (1) axial, supra ventricular, (2) axial, ventricular, (3) axial, eyes, (4) axial, sub-ventricular, (5) sagittal, medial, (6) sagittal, eyes, (7) sagittal, lateral, (8) coronal, ventricular, (9) coronal, non-ventricular, (10) noise, (11) irrelevant slices, (12) partial brain field-of-view, (13) wrap artifact, (14) metal artifact, (15) not brain. As may be appreciated, based on their identification, certain localizer images 200 may be rejected while others are further processed.

For those classifications corresponding to major anatomical portions of the brain, such classifications may also correlate to anatomical landmarks typically references in a brain examination. For example, mid-sagittal plane detection may be performed using the ventricular slices on axial and coronal localizers while the orbits plane may be obtained by using slices containing the eyes. If such relevant slices are not available or the brain coverage in the field-of-view is incomplete (i.e., partial brain field-of-view), then the technologist may be notified to take corrective action, such as moving the field-of-view to get relevant localizer data or changing localizer protocol, etc.

Similarly, the localizer or scout images 200 may contain blank images (e.g., air images) or noise images or extreme slices with irrelevant anatomy. Such unsuitable images are appropriately tagged and not included in the subsequent coverage and orientation estimation.

Figure 11:
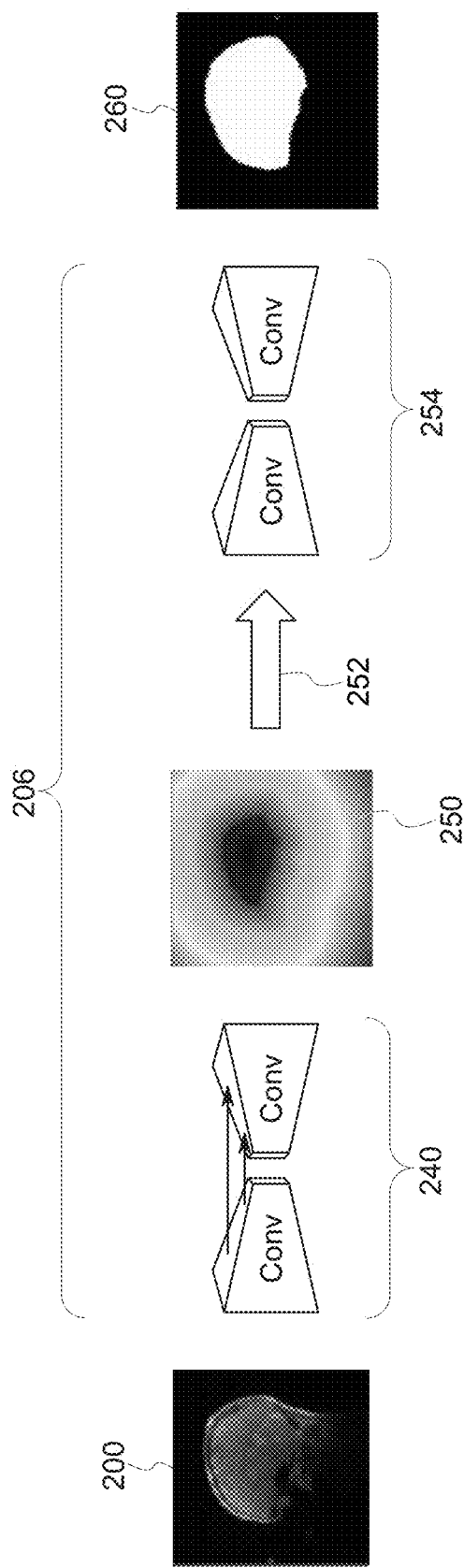
FIG. 11 depicts an example architecture and flow for a coverage network, in accordance with aspects of the present disclosure.

With respect to the coverage network 206, as noted above the coverage network 206 may process the localizer or scout image(s) 200 (or data derived from the localizer or scout images 200) to estimate or predict an anatomic mask (e.g., a brain mask) that corresponds to the desired or needed coverage for a given scan. With this in mind, FIG. 11 provides an example of a deep learning architecture implementation for a brain field-of-view in which the coverage network 206 determines the center and extent of the brain within a localizer or scout image slice 200. In this example, the network utilizes a convolutional neural network (CNN) 240 based UNet architecture. The input to the CNN 240 in this example is a localizer or scout image 200, while the output is Euclidean signed distance transform (SDT) 250 of the resampled brain mask. In this example, the SDT image 250 is thresholded (e.g., >1) at step 252 to obtain a binary mask.

A shape constraint network 254 refines this binary mask 260 to match the ground-truth mask as closely as possible. This shape encoding may help in situations where a protocol or anatomic feature does not match what the network has been trained to process. In particular, the shape encoding provided by the shape constraint network 254 may help address protocol differences between the training data and the data provided when in use and may help ensure consistency with the expected anatomic shape (e.g., head shape) by addressing holes in the image data, spurious leakage, and so forth.

As noted above, in one embodiment the output from the coverage network 206 is provided as an input to a scan plane network 208 used to derive one or more image scan planes to be used in a subsequent diagnostic image scan acquisition. An example of one implementation of such a scan plane network 208 is provided herein to facilitate explanation.

In one implementation, the scan plan network 208 determines one or more scan plane lines with respect to some or all of the input localizer or scout images 200, such as by projecting the different planes onto the 2D localizer or scout images 200 to generate a corresponding 2D plane line on each localizer image. The projected lines are then segmented, such as using a UNet architecture with shape encoder, to generate a segmented binary mask corresponding to the line corresponding to a projected plane on a given localizer or scout image 200. As may be appreciated by, in this manner the projected lines are segmented without segmenting the underlying anatomic structure, i.e., there is no explicit segmentation of landmark or other anatomic structures performed.

In this example, the segmented binary mask corresponding to the projected line on a given localizer image may then be used then used to fit an analytic plane. For example, an analytic plane may be fitted using projected lines in accordance with: $ax+by+cz+d=0$, which fits the segmented lines to a plane equation. Though localizer or scout images 200 are referred to by way of example, as with the coverage network 206, the input to the scan plane network 208 may be the 2D localizer images themselves, an aggregation of the 2D image slice stack treated as 3D volume or a fused 3D image volume.

As discussed herein, different scan plane networks 208 can be trained for each anatomic landmark, such as one network for the anterior commissure and posterior commissure as landmark structures, one network for the optic nerve as a landmark structure, one network for the hippocampus as a landmark structure, one network for the mid-sagittal plane as a landmark structure, and so forth.

Figure 12:
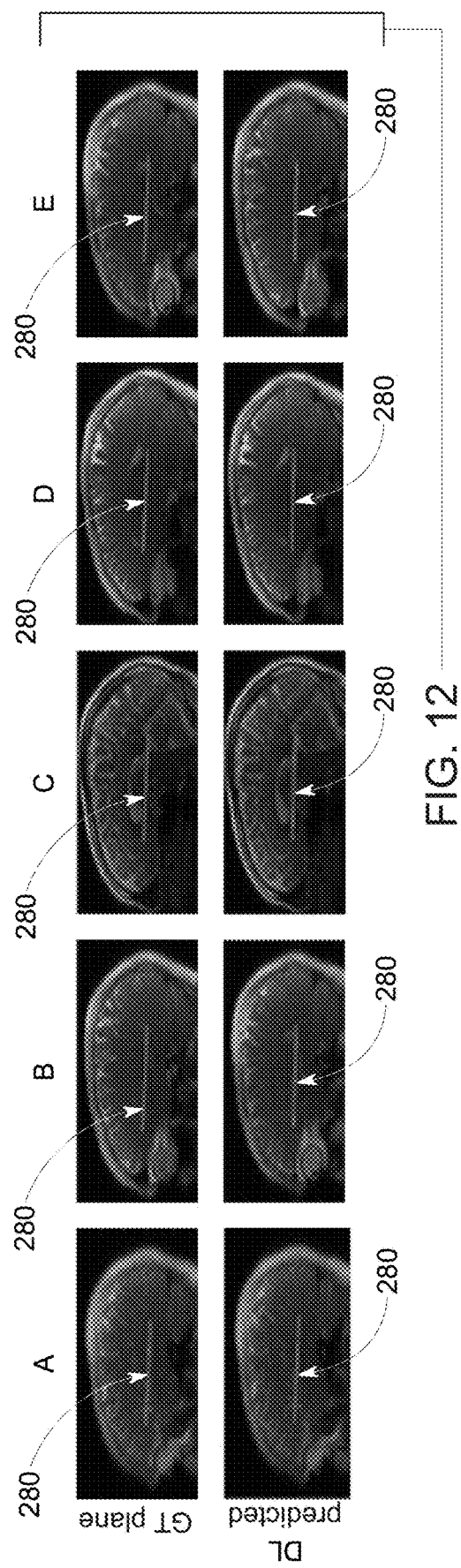
FIG. 12 depicts example images showing ground truth and estimated image scan plane placement, in accordance with aspects of the present disclosure.

An example of this approach in the context of using the anterior commissure and posterior commissure (ACPC) as landmark structures is shown in FIG. 12. Ground truth scan plane placement is shown in the top row of localizer images while scan plan placement estimated using a trained scan plane network 208 as discussed herein is shown in the bottom row of corresponding images. In this example, the ACPC image scan plane 280 is projected on different sagittal slices (denoted A through E). Ideally, the ACPC image scan plane 280 would be predicted using localizer image C (i.e., the middle localizer image slice) since this localizer image contains the AC and PC points. Some localizer images, such as the A, B, and E localizer images, do not contain the necessary anatomic landmarks corresponding to a given scan plane, such as the plane 280 corresponding to ACPC in this example.

In the presently described pipeline, the localizer network 202 would predict this slice (i.e., localizer image C) as most suitable for ACPC scan plane placement and the scan plane 280 would be predicted using this localizer image. However, if this localizer image were corrupted, such as due to pathology, the localizer network 202 would indicate this and ACPC scan plane prediction could still be performed using other relevant localizer images, even though the other localizer images may not contain the exact anatomic landmark points. Indeed, one advantage of the present disclosure compared to explicit segmentation of the landmark anatomic structures is the ability to train the scan plane network 208 to segment the projected image scan planes without the need for the anatomic reference (i.e., landmark) structure being explicitly present in a given localizer image. This may be important in pathological cases, where the structures in question may be modified (e.g., diseased, atrophied, and so forth) or be absent or obscured because of partial volume effects. However, in such instances the disclosed approach will still reliably predict the image scan plane even in the absence or irregularity of the associated landmark anatomic structure.

Figure 13:
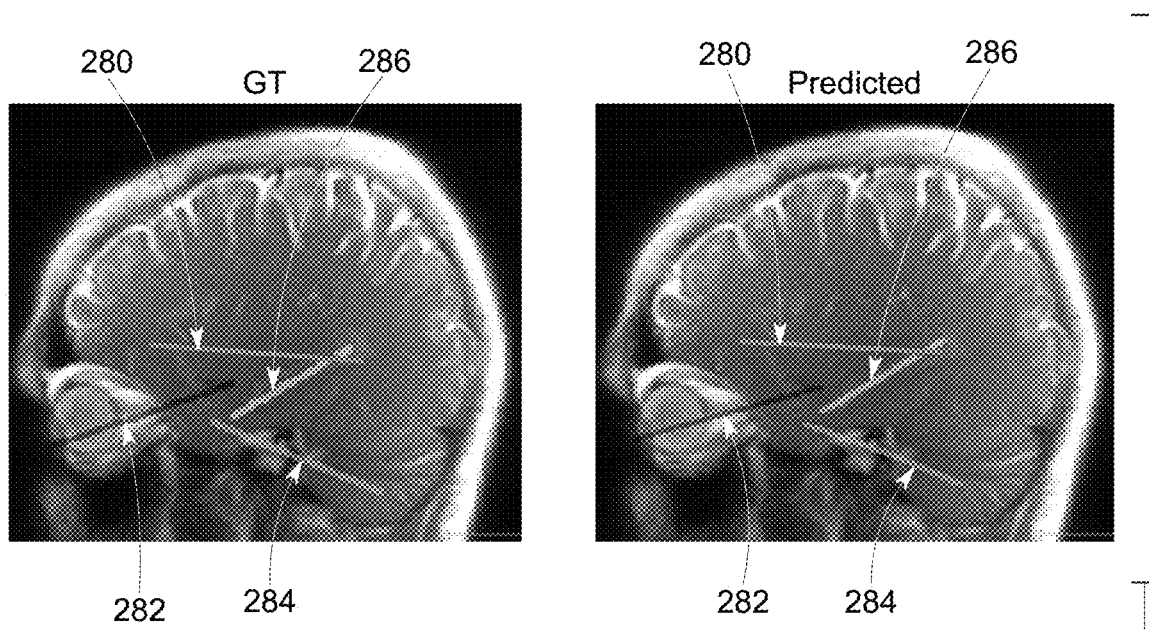
FIG. 13 depicts example images showing ground truth and estimated image scan plane placement, in accordance with aspects of the present disclosure.

While the preceding example describes use of a scan plane network 208 trained to generate a particular image scan plane, in an alternative implementation a given scan plane network 208 may be trained to predict multiple planes concurrently. An example of such an implementation is shown in FIG. 13, in which ground truth scan plane placement for multiple image scan planes-of-interest (here, ACPC image scan plane 280, optical nerve image scan plane 282, internal auditory canal (IAC) image scan plane 284, and hippocampus image scan plane 286) is shown in the top row of localizer images while scan plan placement estimated using a trained scan plane network 208 as discussed herein is shown in the bottom row of corresponding images is shown in the leftmost image while predicted placement of the same scan plane as predicted by a scan plane network 208 is shown on the right.

Figure 14:
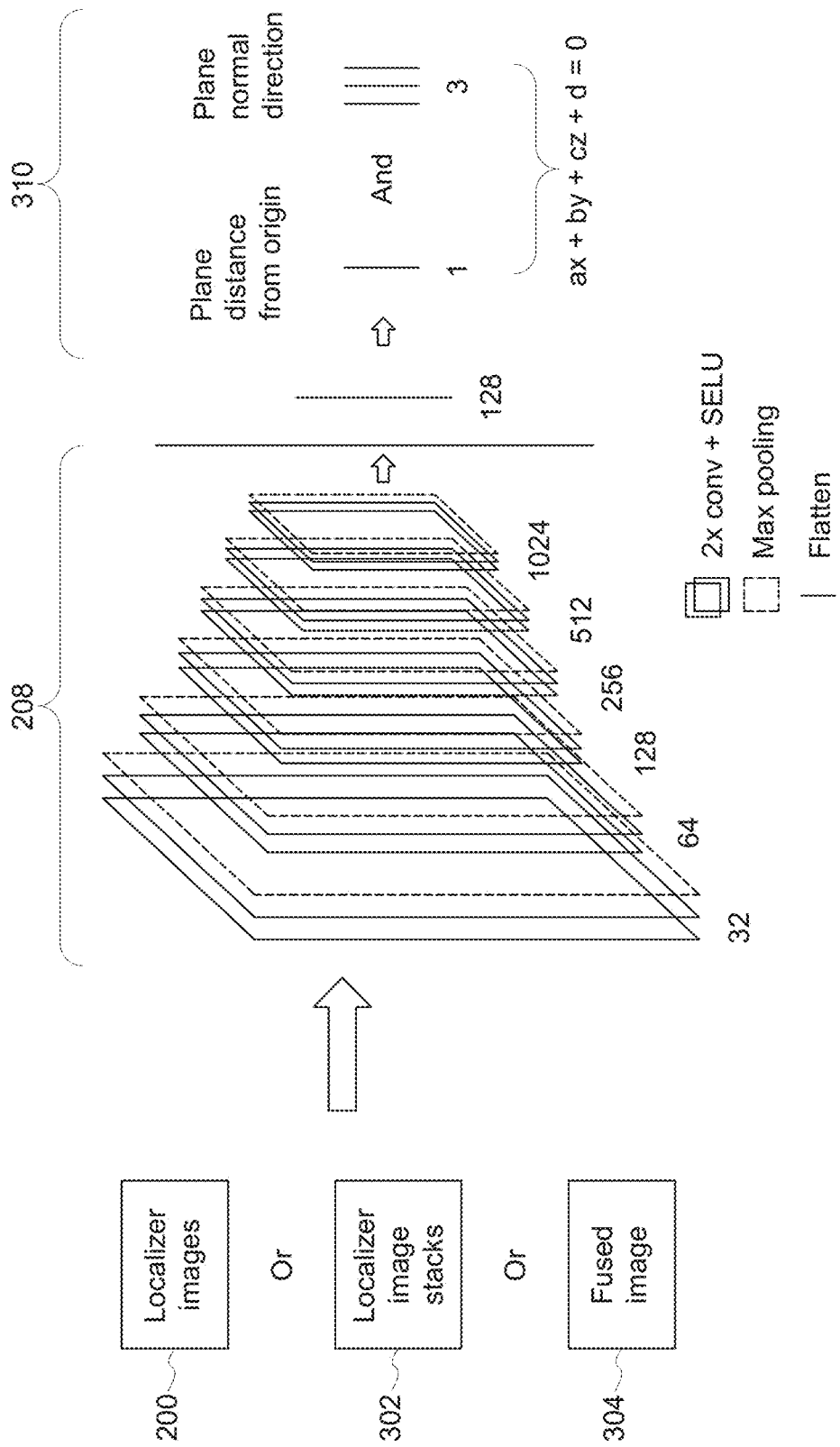
FIG. 14 depicts an example network architecture for estimating image scan plane parameters, in accordance with aspects of the present disclosure.

With the preceding examples related to placing and displaying one or more imaging scan planes for use in a subsequent scanning operation in mind, in an alternative embodiment parameters defining or describing one or more such imaging scan planes may instead be output. An example of one such approach is shown in FIG. 14, where the scan plane network 208 (e.g., a convolutional neural network) is used to directly predict plane parameters 310 (e.g., plane distance from origin, plan normal direction, and so forth) for one or more image scan planes. As in preceding examples, inputs to the trained scan plane network 208 may be one or more localizer images, a stack 302 of such localizer or scout images considered as an aggregate, or a fused image 304 generated from such localizer or scout images 200 (or, not shown, a mask 220 or signed distance transform of the mask 220). As with the preceding embodiments, the scan plane network 208 works directly on the input image or images without segmentation of the anatomic landmarks.

While the preceding examples relate approaches for estimating an image scan plane or parameters for such a plane using localizer or scout images, in another embodiment, localizer or scout images 200 are instead (or in addition) used to evaluate and correct an MRI plane prescription. In particular, in this approach the goal is to ascertain, before the actual data is acquired (i.e., before the diagnostic image acquisition), the performance of the current image scan plane prescription. As may be appreciated, generally image scan plane prescription is done using a set of 2D localizer or scout images 200 or a low-resolution 3D localizer. In both cases, after the image scan plane prescription has been performed (using either manual or automated methods), a user has to wait until the diagnostic image acquisition is performed based on the prescribed image scan plane to ascertain the efficacy of the image scan plane prescription in terms of ability to visualize the landmark region as a contiguous structure. This is especially more relevant with finer structures (e.g., the optic nerve in the brain, ligaments in the knee, and so forth).

With this in mind, in accordance with the present disclosure a deep learning-based framework is proposed to facilitate prospective visualization of the anatomic structures-of-interest and their contiguity prior to performing a diagnostic or primary image acquisition. In one embodiment, synthetic high-resolution images are generated using the localizer or scout image(s) 200. The synthetic images may be used to provide a technologist with a real-time visualize depiction of the anatomic structure-of-interest on reformatted images using the image scan plane prescribed based on the localizer or scout image(s) 200. The technologist may then modify or correct the prescribed image scan plane either: (1) manually with reformat guidance, (2) using a displayed palette of reformatted synthetic high-resolution images to choose the most relevant plane prescription; or (3) automatically determining the correct plane prescription by reformatting the images using different plane prescription parameters and finding the closest matching image for the landmark plane. In this manner the technologist does not have to wait for the higher resolution data (i.e., diagnostic images) to be acquired for ascertaining the efficacy of the image scan plane prescription, which may be defined in terms of ability to visualize the anatomic structure or landmark-of-interest as a contiguous structure in the final imaging volume. Instead, a scan plane-prescription analytic engine can make these changes prospectively.

In this manner, by allowing prospective visualization of the anatomic structure-of-interest through synthetic reformatted images, a technologist may reduce or eliminate unnecessary repeat image examinations and introduce consistency in scans across patients. For algorithm developers, this technique allows capture or the technologist's preferences, such as for use in prediction models for both the image scan plane prediction as well as with respect to the reformatted palette images).

Figure 15:
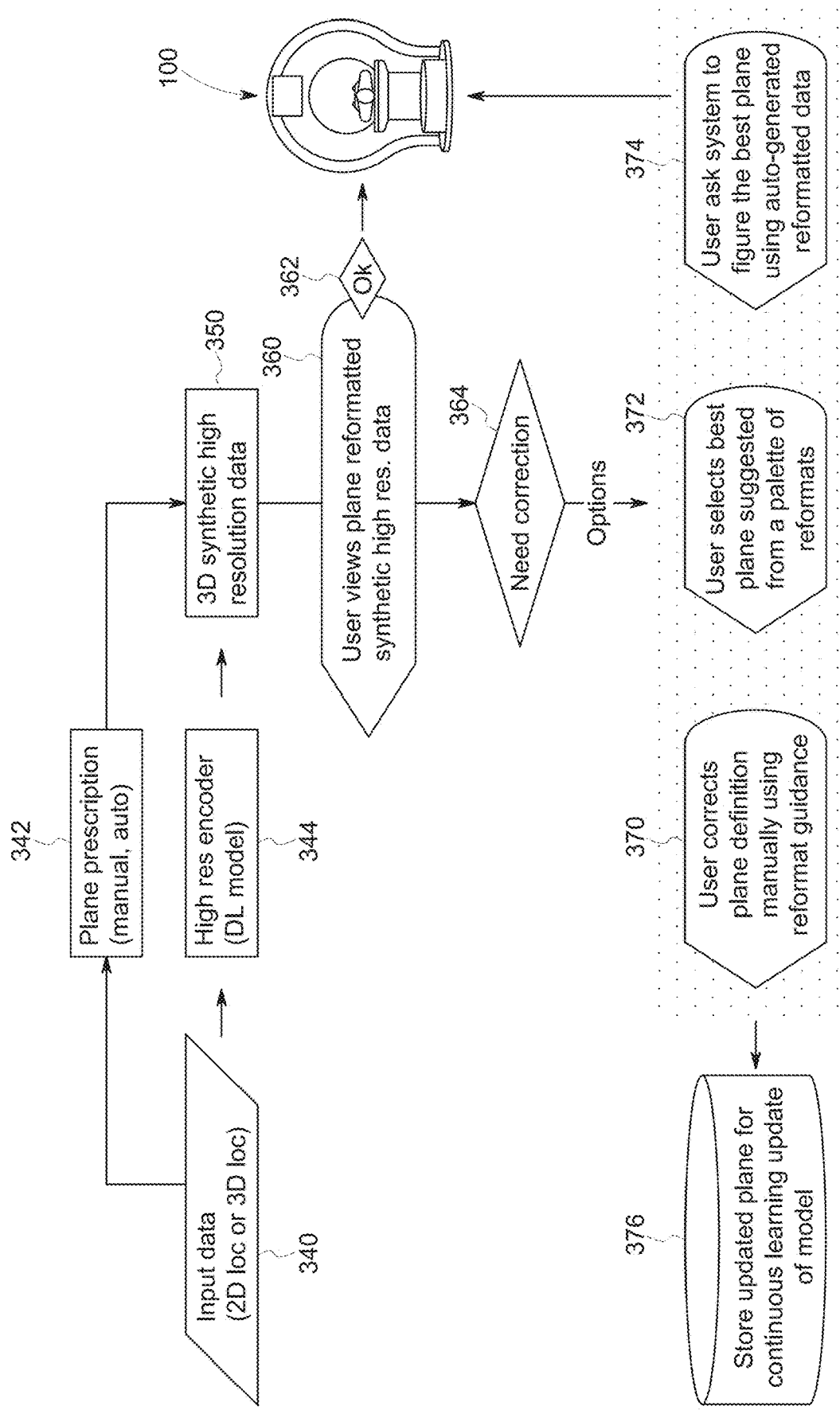
FIG. 15 depicts an example overview of a workflow for evaluating an image scan plane prescription, in accordance with aspects of the present disclosure.

With this in mind, a workflow for the proposed methodology is shown in FIG. 15. As shown in this example, a set of localizer or scout image data 340 (either 2D three-plane localizer or scout images or 3D low-resolution images) are acquired from which the landmark plane-of-interest is to be prescribed. If 2D three-plane localizer or scout images are used as the localizer or scout data 340, such images may be 0.5-1.0 mm in-plane, 10 to 15 mm thickness and acquired using single-shot fast spin echo (SSFSE) or fast gradient-recalled echo (FGRE) protocol. If 3D low resolution images are used as the localizer or scout image data 340, such images may be 1.5-2.5 mm in-plane, 3-5 mm thickness. If 2D three-plane localizer or scout images are acquired, multi-planar localizers can be combined into a single image volume in physical space (i.e., mm space) using interpolation methods to generate a fused 3D image that may be used as the localizer or scout data 340.

The plane prescription 342 may be derived using the localizer or scout data 340 either manually or through automated methods. As discussed herein, the disclosed technique allows the performance of the plane prescription 342 to be ascertained before the actual (e.g., high-resolution, diagnostic) image data is acquired.

In the depicted implementation a deep learning-based algorithm, such as a trained neural network, is used (i.e., as a high-resolution encoder 344) to generate higher resolution three-dimensional (3D) synthetic data 350 from the acquired localizer or scout image data 340. In one embodiment, the high-resolution encoder 344 is deep learning model trained to generate output data in the form of higher resolution imaging data 350 (typically a 3D T1-weighted, T2-weighted or fluid attenuated inversion-recovery (FLAIR) data with 0.5-2 mm isotropic resolution) using lower resolution localizer or scout data 340 as an input. That is, the deep learning super-resolution architecture is trained to map the low-resolution localizer or scout image data 340 to generate synthetic higher resolution images 350.

Once the high-resolution synthetic data 350 is generated it can be used to prospectively to ascertain the fidelity of the imaging data that would be acquired using the plane prescription 342. In particular, the high-resolution synthetic images 350 can be reformatted using the plane prescription 342 parameters to generate synthetic images for the structure-of-interest. This capability to generate structure images may be streamlined to predict a suitable image scan plane to visualize the structure-of-interest.

In the depicted example flow, the technologist is shown (step 360) the prescribed plane 342 and its associated reformatted synthetic imaging volume. If the technologist finds this plane prescription 342 appropriate for the study, then the scan is initiated (decision block 362). If the technologist finds the default plane prescription 342 unsuitable (decision block 364), one or more options may be provided to the technologist.

A first possible option 370 may be to allow the technologist to manually change the plane prescription 342, such as using either a graphical interface or a text interface. In one such embodiment, the technologist may reference the reformatted high-resolution synthetic images 350, which the technologist can review throughout the volume.

Figure 16:
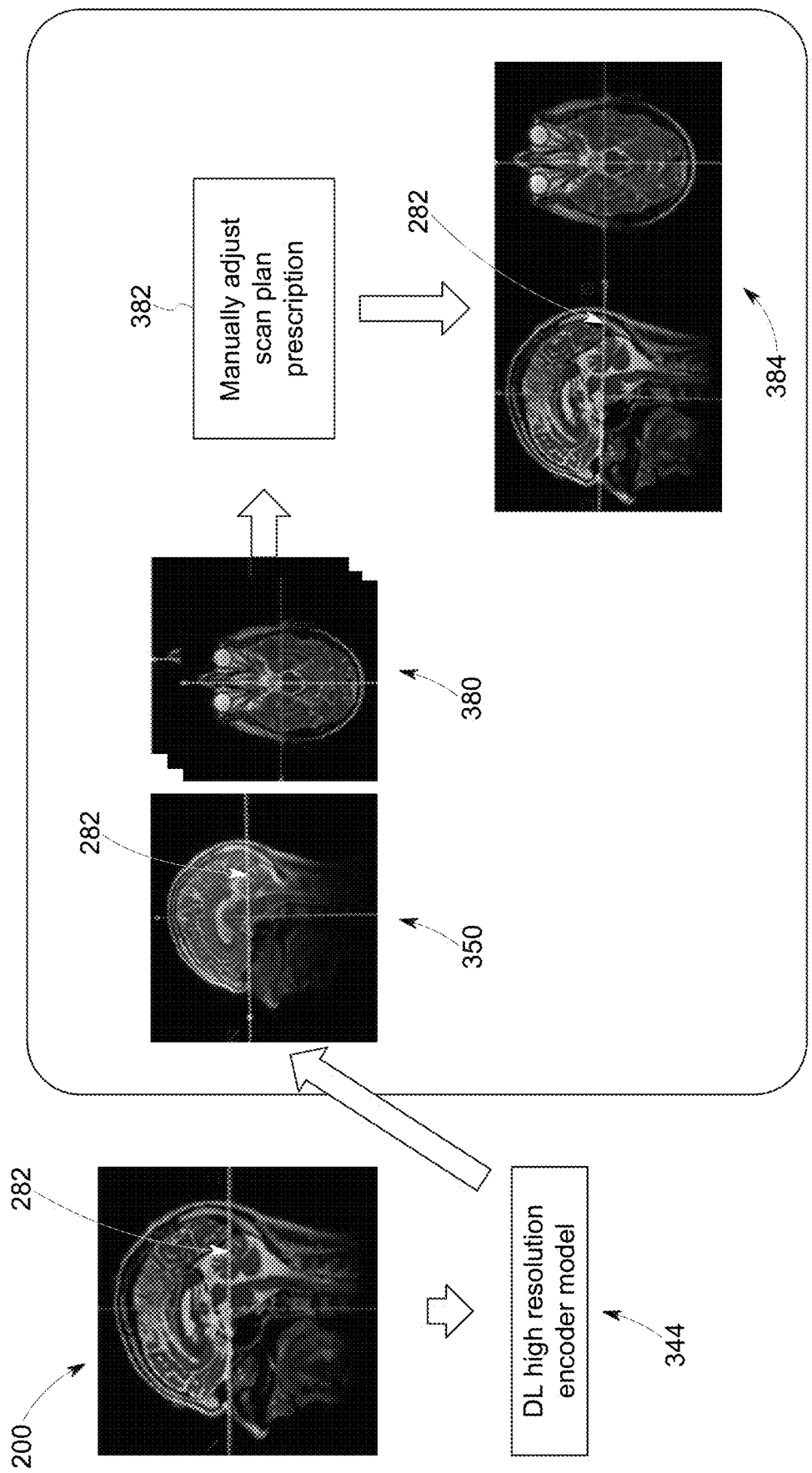
FIG. 16 depicts an example of a manual adjustment to image scan plane prescription, in accordance with aspects of the present disclosure.

The information recording the actions of the technologist and also the corrections made by the technologist can be used to further the training or customization of the neural network to incorporate the new preferences. In such manner, the specific neural network can be customized or personalized for specific technologist, radiologist, or imaging site with the additional data used as continuous learning to retrain the neural network in an automated fashion without manual intervention or atlas-based curation of the new input data Turning to FIG. 16, an example is depicted in which the image scan plane-of-interest is the optic nerve plane 282. The optic nerve plane 282 predicted based upon the localizer images 200 (here provided as the localizer data 340) is illustrated as the input to the process. The deep learning based high-resolution encoder 344 processes the localizer or scout images 200 to generate synthetic high-resolution image data 350 with the predicted optic nerve scan plane. The synthetic high-resolution image data 350 is reformatted based on the predicted plane to generate reformatted high-resolution synthetic images 380 that can be reviewed by the technologist across slices. Upon reviewing the reformatted synthetic image 380, the technologist can manually make adjustments (as shown in block 382) to the image scan plane prescription 342 and visualize the results in the synthetic high-resolution image data in real-time. Based on this review, a modified plane prescription may be determined that provides contiguous landmark anatomic structure visualization in reformatted images and this modified plane prescription may be used to acquire the diagnostic, high-resolution images-of-interest 384.

Figure 17:
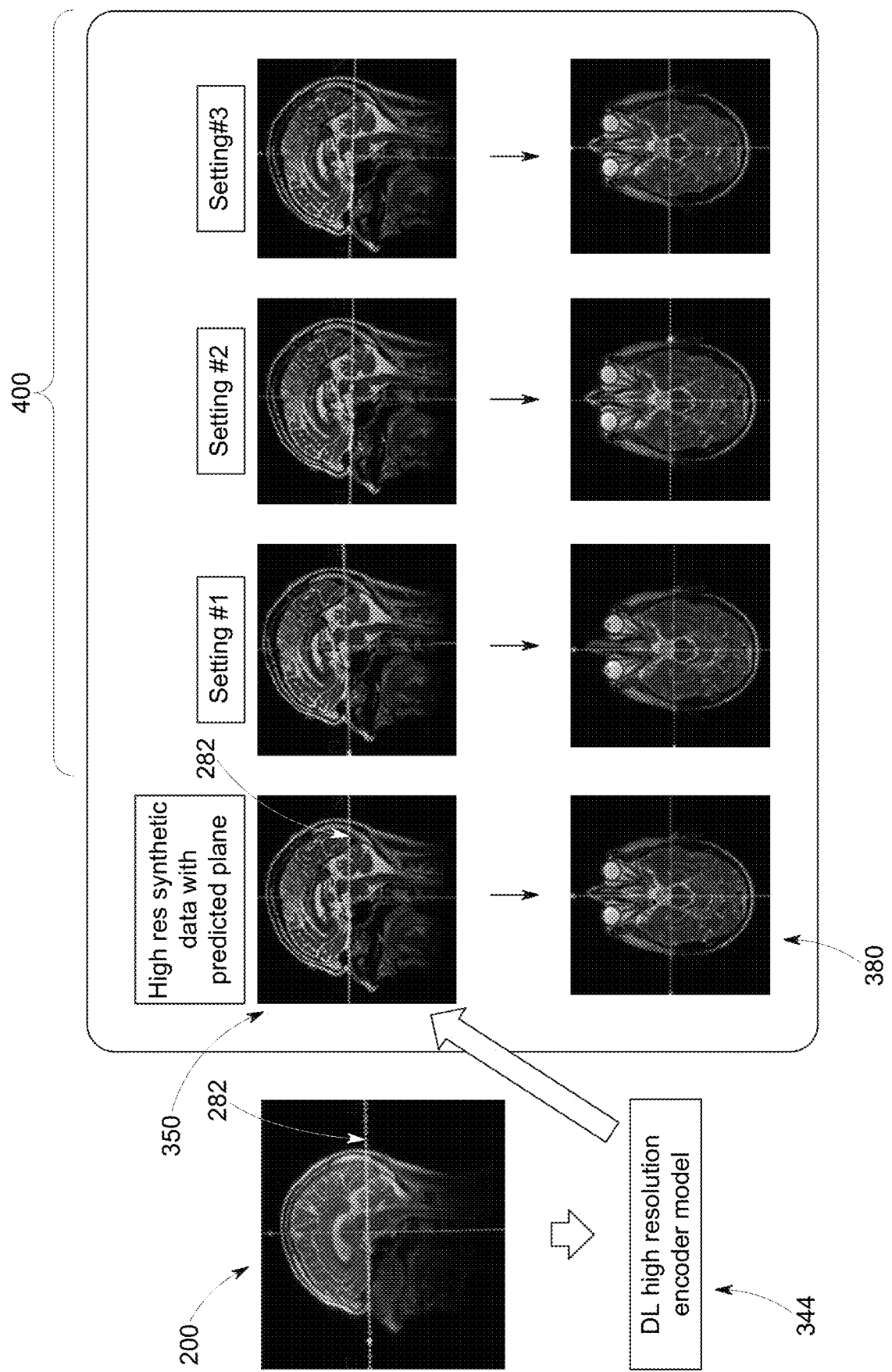
FIG. 17 depicts an example of a palette-based adjustment to image scan plane prescription, in accordance with aspects of the present disclosure.

Alternatively, a second possible option 372 is to display a palette of reformatted synthetic images reflecting potential variations in the scan plane parameterization for the technologist to select from. Turning to FIG. 17, an example is depicted in which the prescribed plane is modulated in the synthetic high-resolution image data 350, 380 to create a palette 400 of reformatted high-resolution synthetic images associated with each of the image scan plane modulations. In the depicted example, the top row of images represents the high-resolution synthetic image data 350 and the bottom row of images depicts the synthetic reformatted axial plane data for review by the technologist. Though only one image/slice is shown in FIG. 17 for each modulation so as to facilitate illustration, in practice multiple slices may be displayed for each reformat to allow a selection to be made based on reviewing the entire volume.

In one such embodiment, the image scan plane modulations can be based on changing prescribed plane parameters along an axis or axes (such as in-plane rotation) or shifting the center point coordinates. Alternatively, one of the planes shown in the palette 400 can be based on a relationship with one or more other landmarks (such as based on a priori statistics. For example, in the brain the optic nerve plane 282 makes an angle of 10 degrees with respect to AC-PC plane. In this implementation, the technologist selects the most suitable image(s) from the palette 400, such as the image(s) which best display the anatomic landmark-of-interest contiguously. Based on the selection from the palette 400 a modified plane prescription may be determined and this modified plane prescription may be used to acquire the diagnostic, high-resolution images-of-interest 384.

Figure 18:
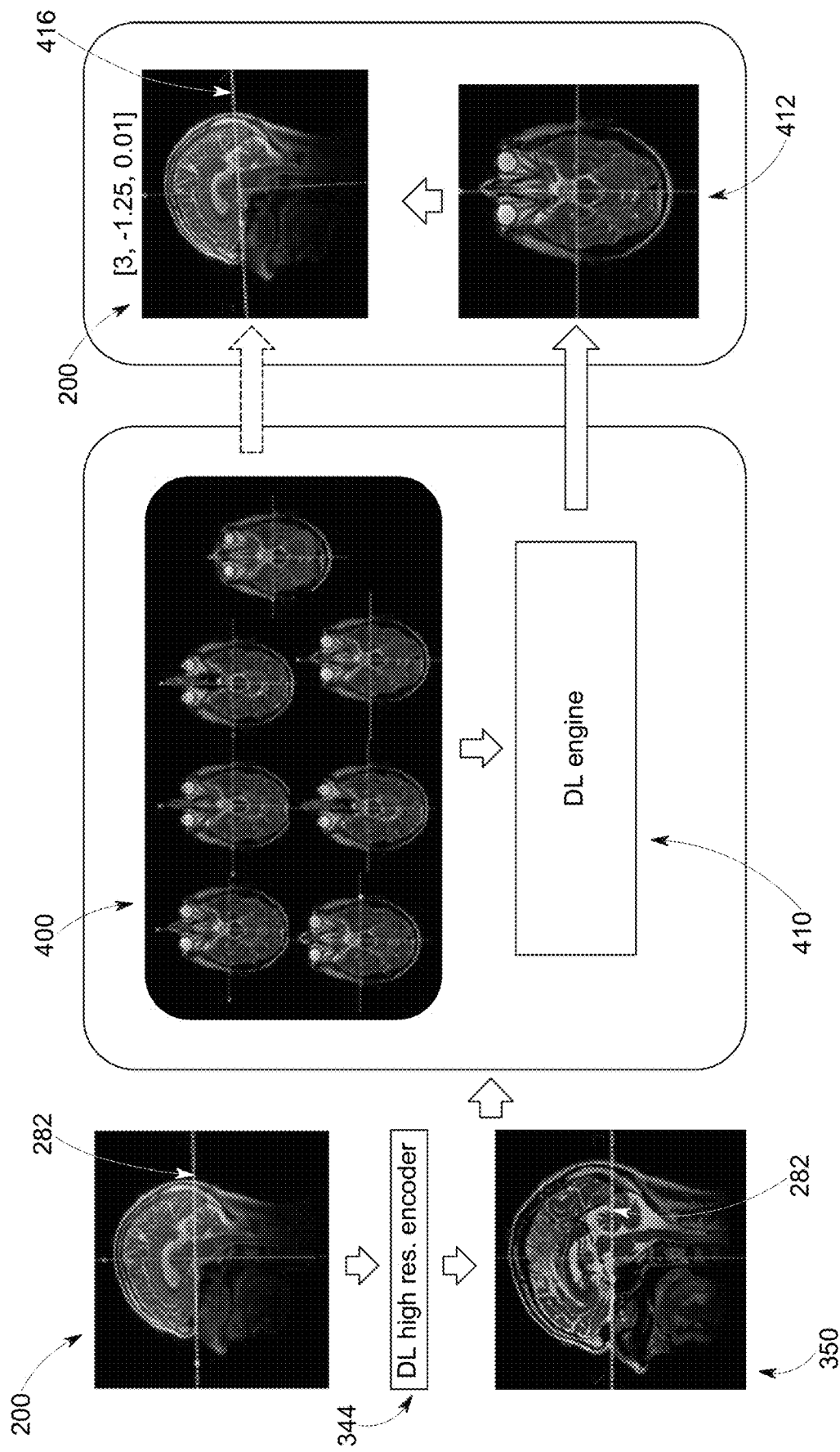
FIG. 18 depicts an example of a deep-learning based adjustment to image scan plane prescription, in accordance with aspects of the present disclosure.

Alternatively, a third possible option 374, shown in FIG. 18, builds upon aspects of the preceding embodiment and automatically modulates the current plane prescription as described above to generate a palette of reformatted synthetic images reflecting potential variations in the scan plane parameterization. However, instead of the palette 400 being reviewed by a technologist, a trained selection neural network (deep learning engine 410) is used to evaluate the palette 400 and to determine the reformatted image data (i.e., selected reformatted data 412) which matches the structure-of-interest. The appropriate plane prescription for matching the selected reformatted data 412 is used in place of or to modify the plane prescription 342 (as shown in the updated plane prescription 416 on the localizer image 200) for subsequent acquisition of the diagnostic or actual high-resolution images data.

Turning back to FIG. 15, the user or system selection with respect to acceptance or modification of the plane prescription 342 may be stored (step 376), such as in a database, and may be used for understanding site preferences and/or updating the model for greater predictive power and increased efficiency.

Technical effects of the invention include translating a clinical scan plane prescription into algorithm facilitated scan plane prescription. One advantage would be the ability to prescribe even finer landmarks on localizer images, which previously required usage of higher resolution images, thereby resulting in significant savings in MRI scan plane prescription. Further, the ability to provide a consistent scan plane reduces the time to read the scan, especially in longitudinal follow-up of patients. Currently the dearth of trained technicians means that exam set-up in multi-planar scan enabling modalities such as MRI is time-consuming tasks and results in significant increase in intra-series, intra-exam and intra-patient gap time. Lastly, a technical effect of certain of the present embodiments is the ability to determine a scan plane, or parameters for a scan plane, without explicit segmentation or identification of the reference anatomic landmark structure. Instead, the entire image may be processed using a trained neural network (or other deep learning-based construct) to determine the scan plane or its parameters without identification or segmentation of the reference landmark anatomy.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for imaging an anatomic region of a patient, comprising:
    acquiring a plurality of two-dimensional (2D) three-plane localizer images of the patient using a magnetic resonance imaging (MRI) system;
    providing the plurality of 2D three-plane localizer images to a localizer network trained to select a subset of the 2D three-plane localizer images for detection of an anatomy-of-interest based on the image contents of the plurality of 2D three-plane localizer images, wherein the localizer network is trained to select a respective 2D three-plane localizer image having the maximal coverage of the anatomy-of-interest;
    processing the subset of 2D three-plane localizer images using a scan plane network trained to determine one or more image scan planes or image scan plane parameters for the anatomy-of-interest, wherein the localizer network and the scan plane networks are separate from each other;
    generating one or more diagnostic images of the anatomic region of the patient using the MRI system based on the one or more image scan planes or image scan plane parameters; and
    wherein the anatomy-of-interest is not segmented prior to determining the one or more image scan planes or image scan plane parameters.

2. The method of claim 1, wherein the plurality of 2D three-plane localizer images are acquired as part of a pre-acquisition step prior to acquisition of one or more diagnostic images.

3. The method of claim 1, wherein one or both of the localizer network or scan plane network are trained using pairs of 2D three-plane localizer images and corresponding diagnostic images acquired based on the plurality of 2D three-plane localizer images, wherein the diagnostic images include data specifying an image scan plane prescription with respect to the associated 2D three-plane localizer image.

4. The method of claim 1, wherein the subset of 2D three-plane localizer images, prior to processing by the scan plane network, are processed by a coverage network trained to identify an imaging field-of-view associated with the anatomy-of-interest.

5. The method of claim 4, wherein the coverage network generates a binary coverage mask as part of identifying the imaging field-of-view.

6. The method of claim 1, wherein the scan plane network determines the one or more image scan planes or image scan plane parameters by fitting an analytic plane to a plane mask encompassing the anatomy-of-interest in the subset of 2D three-plane localizer images generated from the plurality of 2D three-plane localizer images.

7. The method of claim 1, wherein the plurality of 2D three-plane localizer images include 2D axial plane localize images, 2D sagittal plane localizer images, and 2D coronal plane localizer images.

8. A magnetic resonance imaging (MRI) system comprising:
    a memory encoding processor-executable routines for determining one or more imaging scan planes;
    a processing component configured to access the memory and execute the processor-executable routines, wherein the routines, when executed by the processing component, cause the processing component to:
        acquire a plurality of two-dimensional (2D) three-plane localizer images of a patient;
        process the plurality of 2D three-plane localizer images using a localizer network trained to select a subset of the 2D three-plane localizer images for detection of an anatomy-of-interest based on the image contents of the plurality of 2D three-plane localizer images, wherein the localizer network is trained to select a respective 2D three-plane localizer image having the maximal coverage of the anatomy-of-interest;
        process the subset of the 2D three-plane localizer images using a scan plane network trained to determine one or more image scan planes or image scan plane parameters that contain regions of the anatomy-of-interest, wherein the localizer network and the scan plane networks are separate from each other;
        generate one or more diagnostic images of an anatomic region of the patient using the one or more image scan planes or image scan plane parameters; and
        wherein the anatomy-of-interest is not segmented prior to determining the one or more image scan planes or image scan plane parameters.

9. The MRI system of claim 8, wherein the subset of 2D three-plane localizer images, prior to processing by the scan plane network, are processed by a coverage network trained to identify an imaging field-of-view associated with the anatomy-of-interest or a related anatomic structure.

10. The MRI system of claim 8, wherein the plurality of 2D three-plane localizer images are acquired as part of a pre-acquisition step prior to acquisition of one or more diagnostic images.

11. The MRI system of claim 8, wherein the scan plane network determines the one or more image scan planes or image scan plane parameters by fitting an analytic plane to a plane mask encompassing the anatomy-of-interest in the subset of 2D three-plane localizer images generated from the plurality of 2D three-plane localizer images.

* * * * *